United States Patent
Widenhouse et al.

(10) Patent No.: US 11,439,406 B2
(45) Date of Patent: Sep. 13, 2022

(54) CLIP APPLIER

(71) Applicant: AtriCure, Inc., Mason, OH (US)

(72) Inventors: Christopher Widenhouse, Mason, OH (US); Frank Fago, Mason, OH (US); Jonathan McHale, Mason, OH (US); Edward Biehle, Mason, OH (US); Heidi Koett, Mason, OH (US); Erica Schwab, Mason, OH (US)

(73) Assignee: AtriCure, Inc., Mason, OH (US)

( * ) Notice: Subject to any disclaimer, the term of this patent is extended or adjusted under 35 U.S.C. 154(b) by 172 days.

(21) Appl. No.: 16/190,417

(22) Filed: Nov. 14, 2018

(65) Prior Publication Data

US 2019/0142428 A1 May 16, 2019

Related U.S. Application Data

(60) Provisional application No. 62/611,247, filed on Dec. 28, 2017, provisional application No. 62/586,020, filed on Nov. 14, 2017.

(51) Int. Cl.
| | |
|---|---|
| *A61B 17/128* | (2006.01) |
| *A61B 17/00* | (2006.01) |
| *A61B 17/29* | (2006.01) |

(52) U.S. Cl.
CPC ........ *A61B 17/128* (2013.01); *A61B 17/1285* (2013.01); *A61B 2017/0023* (2013.01);
(Continued)

(58) Field of Classification Search
CPC .............. A61B 17/128; A61B 17/1285; A61B 2017/0023; A61B 2017/00243;
(Continued)

(56) References Cited

U.S. PATENT DOCUMENTS

| | | | |
|---|---|---|---|
| 5,240,163 | A | 8/1993 | Stein et al. |
| 5,287,949 | A | 2/1994 | Kitamura |

(Continued)

FOREIGN PATENT DOCUMENTS

| | | | | |
|---|---|---|---|---|
| CA | 2566926 | A1 * | 11/2001 | ............. A61B 18/02 |
| EP | 3117782 | | 1/2017 | |

(Continued)

OTHER PUBLICATIONS

European Patent Office, Extended European Search Report in EP 18879321, dated Sep. 23, 2021, 12 pages.

(Continued)

*Primary Examiner* — Kelly J Bekker
*Assistant Examiner* — Andrew P. Restaino
(74) *Attorney, Agent, or Firm* — Dorton & Willis LLP; Ryan Willis

(57) ABSTRACT

Medical devices and instruments, particularly appliers that may be used to apply occlusion devices such as occlusion clips on anatomical structures, are disclosed. Some example clip appliers may include an activation lever configured to open and close an occlusion clip releasably mounted in an end effector. Some example clip appliers may include a deployment trigger configured to release the occlusion clip from the end effector. Some example clip appliers may include a shaft extending between a handle and the end effector that is rotatable and/or bendable.

9 Claims, 20 Drawing Sheets

(52) U.S. Cl.
 CPC ............. *A61B 2017/0046* (2013.01); *A61B 2017/00243* (2013.01); *A61B 2017/00367* (2013.01); *A61B 2017/00477* (2013.01); *A61B 2017/2912* (2013.01); *A61B 2017/2929* (2013.01)

(58) Field of Classification Search
 CPC .. A61B 2017/00367; A61B 2017/0046; A61B 2017/00477; A61B 2017/2912; A61B 2017/2929; A61B 2017/00371; A61B 2017/2916; A61B 2017/2919; A61B 2017/320094
 See application file for complete search history.

(56) References Cited

U.S. PATENT DOCUMENTS

| | | |
|---|---|---|
| 5,582,615 A | 12/1996 | Foshee et al. |
| 2001/0034536 A1 | 10/2001 | Looper |
| 2002/0082615 A1 | 6/2002 | Shipp et al. |
| 2005/0119677 A1 | 6/2005 | Shipp |
| 2009/0182352 A1* | 7/2009 | Paz ............... A61B 17/0682 606/143 |
| 2010/0076260 A1 | 3/2010 | Taylor |
| 2013/0131649 A1 | 5/2013 | Hughett, Sr. |
| 2013/0190777 A1 | 7/2013 | Hughett, Sr. |
| 2013/0296848 A1 | 11/2013 | Allen, IV |
| 2016/0038341 A1 | 2/2016 | Clopp et al. |
| 2016/0157926 A1 | 6/2016 | Boudreaux |
| 2017/0014135 A1 | 1/2017 | Martin |
| 2017/0105746 A1* | 4/2017 | O'Keefe .......... A61B 17/00234 |

FOREIGN PATENT DOCUMENTS

| | | |
|---|---|---|
| WO | 2010011661 | 1/2010 |
| WO | PCT/US18/60955 | 2/2019 |

OTHER PUBLICATIONS

European Patent Office, Partial European Search Report in EP 18879321, dated Jun. 22, 2021, 13 pages.
European Patent Office, examination report in EP 18879321.0, dated Jul. 29, 2022, 4 pages.

* cited by examiner

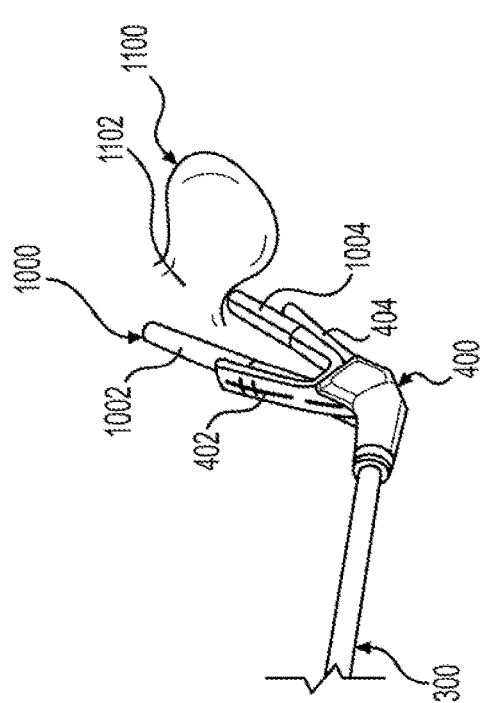
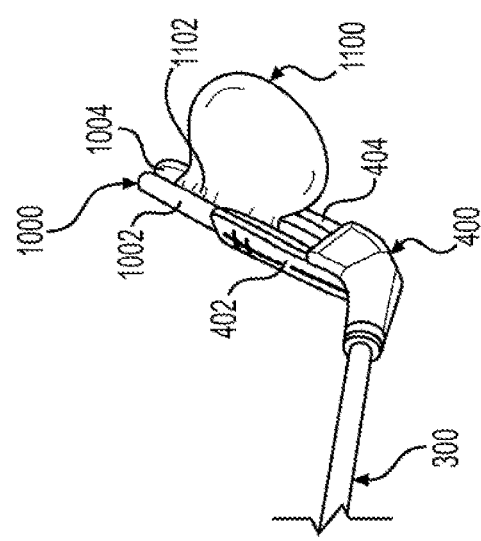
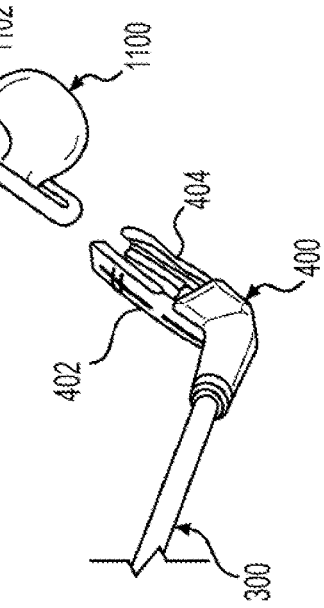
FIG. 3
FIG. 4
FIG. 5

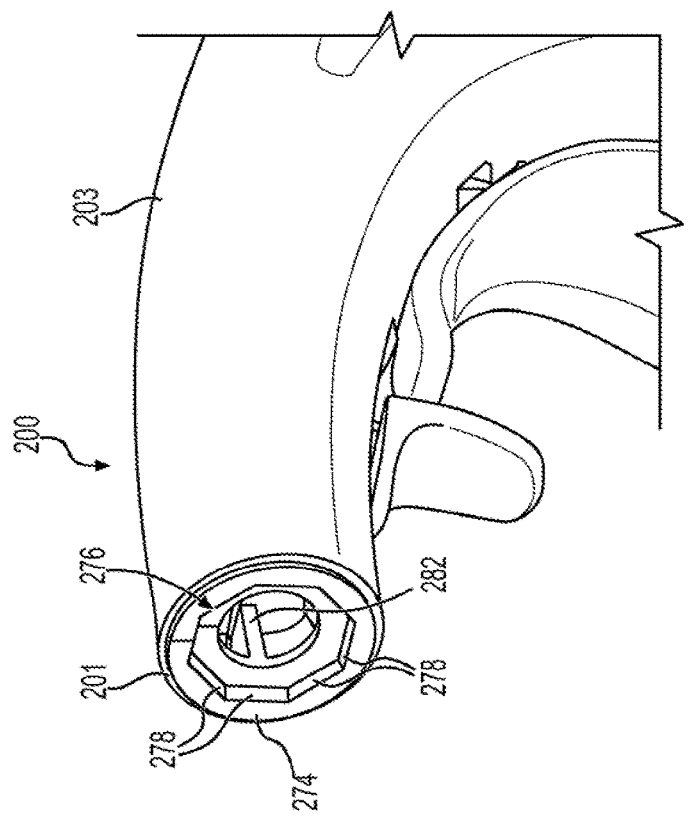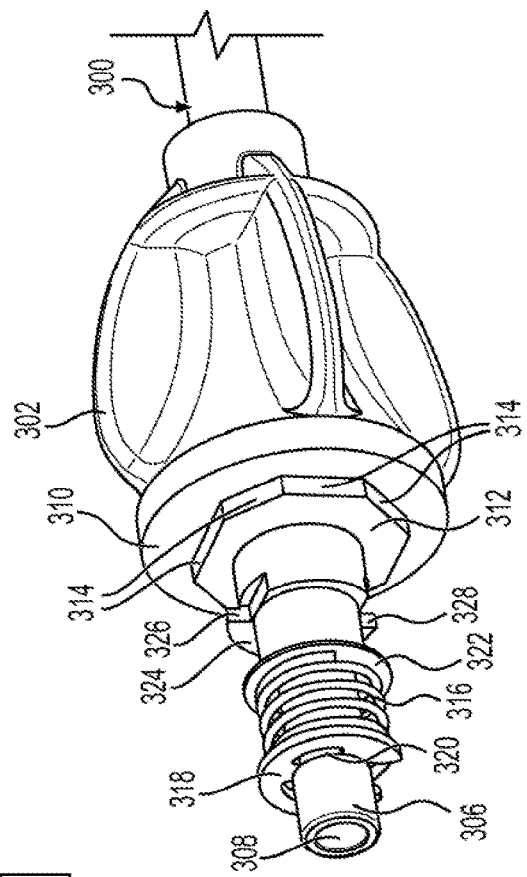

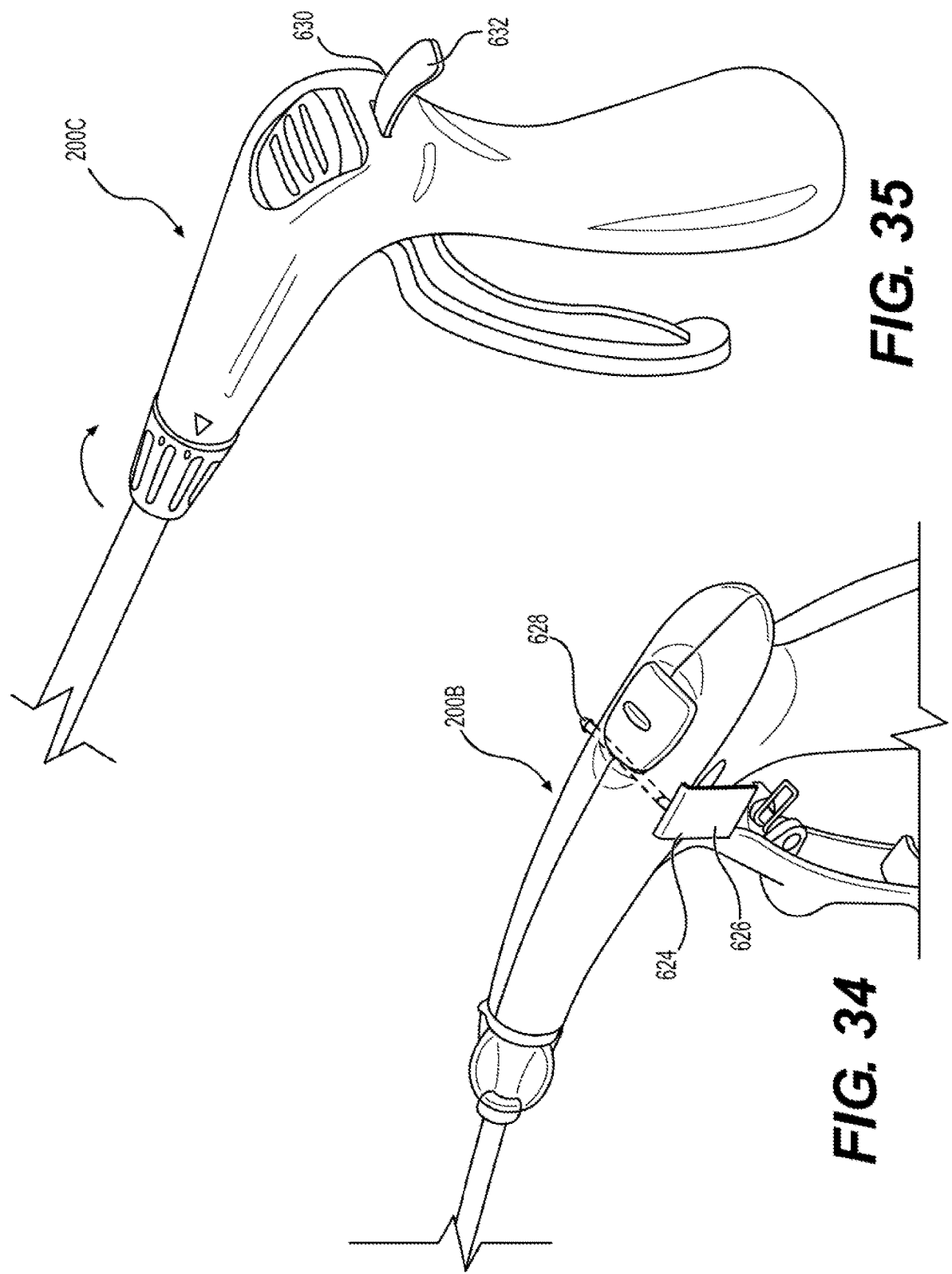

CLIP APPLIER

CROSS REFERENCE TO RELATED APPLICATIONS

This application claims the benefit of U.S. Provisional Application No. 62/586,020, filed Nov. 14, 2017, and U.S. Provisional Application No. 62/611,247, filed Dec. 28, 2017, which are incorporated by reference.

INTRODUCTION TO THE INVENTION

The present disclosure is directed to medical instruments and devices, and, more specifically, to appliers that may be used to apply occlusion devices on anatomical structures, such as an occlusion clip on a left atrial appendage of a heart.

It is a first aspect of the present disclosure to provide a medical instrument which may include a handle; an activation lever disposed on the handle, the activation lever being movable between a closed activation lever configuration and an open activation lever configuration by application of an external force to the activation lever; a shaft mounted to and extending distally from the handle; and/or an end effector disposed distally on the shaft. The end effector may include a first jaw movable between a closed jaw configuration and an open jaw configuration. The first jaw may be operatively coupled to the activation lever such that moving the activation lever from the closed activation lever configuration to the open activation lever configuration moves the first jaw from the closed jaw configuration to the open jaw configuration. The activation lever and handle may include a track and a track follower configured to decrease an external force required to move the activation lever from the closed activation lever configuration to the open activation lever configuration as the activation lever moves from the closed activation lever configuration to the open activation lever configuration. The first jaw may be configured to releasably receive an occlusion clip.

In a more detailed embodiment of the first aspect, an external force required to maintain the activation lever in the open activation lever configuration may be less than the external force required move the activation lever from the closed activation lever configuration to the open activation lever configuration. The external force required to maintain the activation lever in the open activation lever configuration may be less than about one half of the external force required move the activation lever from the closed activation lever configuration to the open activation lever configuration. An external force required move the activation lever from the closed activation lever configuration to the open activation lever configuration may be substantially constant for about 85% of a length of travel from the closed activation lever configuration to the open activation lever configuration. The activation lever may be pivotably disposed on the handle and/or the first jaw may be pivotably disposed on the end effector. The activation lever may be operatively coupled to the first jaw by an activation cable extending through the shaft.

In a more detailed embodiment of the first aspect, the medical instrument may include a linkage including a first end pivotably attached to the activation lever and a second end having the track follower affixed thereto. The track may be disposed within the handle and/or may be configured to slidably receive the track follower. The activation cable may be mounted to the second end of the linkage and extends to the end effector through a channel in the shaft. Moving the activation lever between the closed activation lever configuration and the open activation lever configuration by application of the external force to the activation lever may move the track follower along the track from a first location to a second location. Moving the track follower from the first location to the second location may pull the activation cable generally proximally. Pulling the activation cable proximally may cause the end effector to move the first jaw from the closed jaw configuration to the open jaw configuration. The track may be generally arcuately shaped. A pivot point of the activation lever, a direction of the activation cable generally between the second end of the linkage and the pivot point of the activation lever, and the track follower may be generally aligned when the activation lever is in the open activation lever configuration.

In a more detailed embodiment of the first aspect, the medical instrument may include a spring operatively coupled to the activation lever and the linkage to bias the activation lever towards the closed activation lever configuration. The medical instrument may include an occlusion clip releasably attached to the end effector. The occlusion clip may move from a closed occlusion clip configuration to an open occlusion clip configuration as the first jaw moves from the closed jaw configuration to the open jaw configuration. The occlusion clip may be an open-ended occlusion clip. The occlusion clip may be biased toward the closed occlusion clip configuration. When the activation lever is in the open activation lever position and the external force is removed, the activation lever may move to the closed activation lever position, the track follower may move from the second location to the first location, and the first jaw may move from the open jaw configuration to the closed jaw configuration without application of an external force.

In a more detailed embodiment of the first aspect, the shaft may be mounted to the handle such that the shaft is selectively rotatable relative to the handle. the handle and the shaft may each include a releasably engageable corresponding locking feature arranged to selectively inhibit rotation of the shaft relative to the handle.

In a more detailed embodiment of the first aspect, the shaft may be plastically deformable. The shaft may be plastically deformable up to an angle of at least about 45 degrees.

In a more detailed embodiment of the first aspect, the medical instrument may include an occlusion clip releasably attached to the end effector and/or a deployment trigger disposed on the handle. The deployment trigger may be movable between a pre-deployment configuration and a deployment configuration by application of an external force to the deployment trigger. The deployment trigger may be operable to release the occlusion clip from the end effector.

In a more detailed embodiment of the first aspect, the medical instrument may include a deployment cable extending from the handle to the first jaw. The deployment cable may be operative, when retracted, to release an occlusion clip from the first jaw. The medical instrument may include at least one of a thumbwheel disposed on the handle, the thumbwheel being operable to retract the deployment cable and release the occlusion clip; a deployment lever disposed on the handle, the deployment lever being operable to retract the deployment cable and release the occlusion clip; a rotatable pull tab disposed on the handle, the pull tab being operable, after being rotated, to retract the deployment cable and release the occlusion clip; or a torsion spring cable retractor comprising a torsion spring arranged to apply proximal tension on deployment cable and a retainer arranged to selectively prevent retraction of deployment cable until the retainer is disengaged, the torsion spring cable retractor being operable to retract the deployment cable and release the occlusion clip.

It is a second aspect of the present disclosure to provide s medical instrument including a handle; a deployment trigger disposed on the handle, the deployment trigger being movable between a pre-deployment configuration and a deployment configuration by application of an external force to the deployment trigger; a shaft mounted to and extending distally from the handle; and/or an end effector disposed distally on the shaft, the end effector comprising a first jaw configured to releasably receive an occlusion clip, the deployment trigger being operatively coupled to the first jaw by a deployment cable. Moving the deployment trigger from the pre-deployment configuration to the deployment configuration may retract the deployment cable proximally, releasing the occlusion clip from the first jaw.

In a more detailed embodiment of the second aspect, the medical instrument may include an elastic member disposed within the handle. The elastic member may include a first end and a second end, the second end being affixed to the handle. The deployment cable may extend from the first end of the elastic member to the first jaw. When the deployment trigger is in the pre-deployment configuration, the elastic member may be held in an extended configuration. When the deployment trigger is moved to the deployment configuration, the elastic member may retract the deployment cable proximally. Retracting the deployment cable proximally may release the occlusion clip from the first jaw. The elastic member may be an extension spring.

In a more detailed embodiment of the second aspect, the medical instrument may include a stop member affixed to the deployment cable between the first end of the elastic member and the shaft; and/or an anchoring plate disposed within the handle and arranged to selectively block proximal movement of the stop member. When the deployment trigger is in the pre-deployment configuration, the elastic member may be held in the extended configuration by the stop member abutting a distal surface of an anchoring plate. The medical instrument may include a deployment trigger slot disposed on the deployment trigger, the slot slidably receiving the stop member therein. The anchoring plate may be fixedly mounted to the handle. When the deployment trigger is in the pre-deployment configuration, the deployment trigger slot may be at least partially aligned with the anchoring plate. When the deployment trigger is in the deployment configuration, the deployment trigger slot may be aligned generally adjacent to the anchoring plate, thereby allowing the stop member to move proximally relative to the deployment trigger slot and the anchoring plate. 25. The anchoring plate may include an anchoring plate slot that is wider than the deployment cable and narrower than the stop member. When the deployment trigger is in the pre-deployment configuration, the deployment trigger slot may be generally aligned with the anchoring plate slot.

In a more detailed embodiment of the second aspect, the medical instrument may include a fixed slot disposed on the handle, the slot slidably receiving the stop member therein. The anchoring plate may be movable relative to the fixed slot. The deployment trigger may be operatively coupled to the anchoring plate. When the deployment trigger is in the pre-deployment configuration, the fixed slot may be aligned such that the stop member at least partially abuts the anchoring plate. When the deployment trigger is in the deployment configuration, the fixed slot may be aligned with an opening through the anchoring plate, thereby allowing the stop member to move proximally relative to the fixed slot and at least partially through the opening through the anchoring plate.

In a more detailed embodiment of the second aspect, the medical instrument may include a removable safety tab. The safety tab may include a pin extending into the handle and arranged to prevent movement of the deployment trigger and a grip extending outwardly from the handle.

In a more detailed embodiment of the second aspect, the shaft may be mounted to the handle such that the shaft is selectively rotatable relative to the handle. The handle and/or the shaft may each include a releasably engageable corresponding locking feature arranged to selectively inhibit rotation of the shaft relative to the handle.

In a more detailed embodiment of the second aspect, the shaft may be plastically deformable. The shaft may be plastically deformable up to an angle of at least about 45 degrees.

In a more detailed embodiment of the second aspect, the medical instrument may include an activation lever disposed on the handle. The activation lever may be movable between a closed activation lever configuration and an open activation lever configuration by application of an external force to the activation lever. The end effector may include a first jaw movable between a closed jaw configuration and an open jaw configuration. The first jaw may be operatively coupled to the activation lever such that moving the activation lever from the closed activation lever configuration to the open activation lever configuration moves the first jaw from the closed jaw configuration to the open jaw configuration.

It is a third aspect of the present disclosure to provide a medical instrument including a handle; a plastically deformable shaft mounted to and extending distally from the handle; and/or an end effector disposed distally on the shaft and configured to releasably receive an occlusion clip thereon. The shaft may be mounted to the handle such that the shaft is selectively rotatable relative to the handle.

In a more detailed embodiment of the third aspect, the handle may include a handle locking feature. The shaft may include a shaft locking feature corresponding to the handle locking feature. The handle locking feature and/or the shaft locking feature may be releasably engageable to selectively inhibit rotation of the shaft relative to the handle. Either the handle locking feature or the shaft locking feature may include a locking recess including a plurality of inwardly facing locking recess locking faces. The other of the handle locking feature or the shaft locking feature may include a projecting locking boss including a plurality of radially outwardly facing locking boss faces. In a locked configuration, the locking boss may be at least partially engaged within the locking recess, inhibiting rotation of the shaft relative to the handle. The handle locking feature may include a generally octagonally shaped locking recess disposed on a distal face of the handle. The shaft locking feature may include a generally octagonally shaped, proximally projecting locking boss. The medical instrument may include a spring operatively disposed on the handle and the shaft to bias the shaft and the handle toward the locked configuration.

In a more detailed embodiment of the third aspect, the shaft and/or the handle may include a rotation limiting feature that prevents rotation of the shaft relative to the handle beyond a predetermined maximum amount. The rotation limiting feature may include, on the handle, a generally longitudinally extending bar and/or on the shaft, a stop comprising at least one stop face arranged to engage the bar and prevent further rotation when the shaft is rotated a predetermined maximum amount.

In a more detailed embodiment of the third aspect, the medical instrument may include a friction spring in a press fit engagement with a surface of the shaft, the friction spring including a tab engaging the handle to prevent rotation of the friction spring relative to the handle. The press fit engagement between the friction spring and the surface of the shaft may oppose rotation of the shaft relative to the handle but may allow such rotation when sufficient torque is applied to the shaft.

In a more detailed embodiment of the third aspect, the shaft may include a proximally extending lock projection comprising a plurality of locking faces. The handle may include a locking spring arranged to elastically engage at least one of the locking faces. The elastic engagement of the locking spring and the locking faces may oppose rotation of the shaft relative to the handle but may allow such rotation when sufficient torque is applied to the shaft.

In a more detailed embodiment of the third aspect, the shaft may include at least one of aluminum, copper, stainless steel, and polycarbonate. The shaft may be deformable up to an angle of at least about 45 degrees.

In a more detailed embodiment of the third aspect, the medical instrument may include a deployment trigger disposed on the handle. The deployment trigger may be movable between a pre-deployment configuration and a deployment configuration by application of an external force to the deployment trigger. The deployment trigger may be operable to release an occlusion clip from the end effector.

In a more detailed embodiment of the third aspect, the end effector may include a first jaw movable between a closed jaw configuration and an open jaw configuration. The medical instrument may include an activation lever disposed on the handle. The activation lever may be movable between a closed activation lever configuration and an open activation lever configuration by application of an external force to the activation lever. The first jaw may be operatively coupled to the activation lever such that moving the activation lever from the closed activation lever configuration to the open activation lever configuration moves the first jaw from the closed jaw configuration to the open jaw configuration.

It is a fourth aspect of the present disclosure to provide method of deploying an occlusion clip including placing a clip applier in an open configuration by moving an activation lever of the clip applier from a closed activation lever configuration to an open activation lever configuration by applying an external force to the activation lever; positioning an occlusion clip adjacent to an occlusion site, which includes deforming a shaft of the clip applier, the occlusion clip being releasably held by an end effector of the clip applier; placing the clip applier in the closed configuration by moving the activation lever from the open configuration to the closed configuration; operating a deployment trigger on the clip applier to release the occlusion clip from the end effector; and/or withdrawing the end effector from the occlusion site, leaving the occlusion clip on the occlusion site.

In a more detailed embodiment of the fourth aspect, applying the external force to the activation lever may include decreasing the amount of external force as the activation lever moves from the closed activation lever configuration to the open activation lever configuration. The method may include, while positioning the occlusion clip adjacent to the occlusion site, maintaining the clip applier in the open configuration by continuing to apply the external force on the activation lever, the force required for maintaining the clip applier in the open configuration being less than the external force required for moving the activation lever from the closed activation lever configuration to the open activation lever configuration. The method may include, before operating the deployment trigger to release the occlusion clip from the end effector, placing the clip applier in an open configuration, repositioning the occlusion clip, and/or placing the clip applier in the closed configuration. Operating the deployment trigger to release the occlusion clip from the end effector may include moving a cable stop relative to an anchoring plate to allow the cable stop to slide by the anchoring plate, thereby allowing proximal movement of a deployment cable affixed to the cable stop. The proximal movement of the deployment cable may release the occlusion clip from the end effector. The method may include, before placing a clip applier in an open configuration, rotating a shaft of the clip applier relative to a handle of the clip applier, the end effector being mounted distally on the shaft and the handle being mounted proximally on the shaft. The method may include, before placing a clip applier in an open configuration, plastically deforming a shaft of the clip applier, the end effector being mounted distally on the shaft and the handle being mounted proximally on the shaft.

It is a fifth aspect of the present disclosure to provide a method of deploying an occlusion clip including positioning an occlusion clip adjacent to an occlusion site, the occlusion clip being releasably coupled to an end effector of a clip applier by a deployment cable, the deployment cable extending from the end effector to a handle of the clip applier, the deployment cable having a cable stop fixedly attached thereto; releasing the occlusion clip from the end effector by aligning a slot having the cable stop slidably therein from a pre-deployment configuration generally aligned with an anchoring plate to a deployment configuration to allow a spring attached to the deployment cable to pull the deployment cable proximally; and withdrawing the end effector, leaving the occlusion clip on the occlusion site.

In a more detailed embodiment of the fifth aspect, aligning the slot having the cable stop therein from the pre-deployment configuration generally aligned with the anchoring plate to the deployment configuration may include aligning a movable slot having the cable stop slidably therein from a pre-deployment configuration generally aligned with a fixed anchoring plate to a deployment configuration generally aligned adjacent to the fixed anchoring plate. Aligning the slot having the cable stop therein from the pre-deployment configuration generally aligned with the anchoring plate to the deployment configuration comprises aligning a fixed slot having the cable stop therein from a pre-deployment configuration generally aligned with a movable anchoring plate to a deployment configuration generally aligned through an opening in a movable anchoring plate. The method may include, before releasing the occlusion clip from the end effector, removing a safety tab, the safety tab preventing deployment of the occlusion clip. The method may include, before placing a clip applier in an open configuration, rotating a shaft of the clip applier relative to a handle of the clip applier, the end effector being mounted distally on the shaft and the handle being mounted proximally on the shaft. The method may include, before positioning the occlusion clip adjacent to the occlusion site, plastically deforming a shaft of the clip applier, the shaft having the end effector mounted distally thereon and the handle mounted proximally thereon.

It is a sixth aspect of the present disclosure to provide a method of operating a medical device including rotating and deforming a shaft of a clip applier relative to a handle of the clip applier, the clip applier comprising the handle, the shaft selectively rotatably mounted distally on the handle, and an end effector mounted distally on the shaft, the end effector having an occlusion clip releasably mounted thereto; positioning the occlusion clip adjacent to an occlusion site; deploying the occlusion clip from the end effector by actuating a deployment trigger on the handle; and/or withdrawing the end effector, leaving the occlusion clip on the occlusion site.

In a more detailed embodiment of the sixth aspect, a rotating the shaft of the clip applier relative to the handle of the clip applier may include disengaging a shaft locking feature from a handle locking feature, rotating the shaft relative to the handle, and/or engaging the shaft locking feature with the handle locking feature. Disengaging a shaft locking feature from a handle locking feature may include applying a generally distal force on the shaft and/or moving the shaft distally relative to the handle. Engaging the shaft locking feature with the handle locking feature may include releasing the generally distal force on the shaft and/or allowing a spring to pull the shaft proximally toward the handle.

In a more detailed embodiment of the sixth aspect, rotating the shaft relative to the handle may include rotating the shaft relative to the handle until a rotation limiting feature prevents further rotation.

In a more detailed embodiment of the sixth aspect, the method may include, before positioning the occlusion clip adjacent to the occlusion site, plastically deforming the shaft. The method may include, before positioning the occlusion clip adjacent to the occlusion site, placing the clip applier in an open configuration by moving an activation lever of the clip applier from a closed activation lever configuration to an open activation lever configuration by applying an external force to the activation lever; and/or before deploying the occlusion clip from the end effector, placing the clip applier in the closed configuration by moving the activation lever from the open configuration to the closed configuration. The occlusion clip may be releasably mounted to the end effector by a deployment cable, the deployment cable extending from the end effector, through the shaft, and to the handle. The deployment cable may be coupled to an extended extension spring within the handle. A cable stop may be disposed on the deployment cable. Actuating a deployment trigger on the handle may include aligning a movable slot having the cable stop slidably therein from a pre-deployment configuration generally aligned with a fixed anchoring plate to a deployment configuration generally aligned adjacent to the fixed anchoring plate, thereby allowing the cable stop to move by the anchoring plate, and allowing the spring to retract the deployment cable.

It is a seventh aspect of the present disclosure to a method of deploying an occlusion clip including placing a clip applier in an open configuration by moving an activation lever of the clip applier from a closed activation lever configuration to an open activation lever configuration by applying an external force to the activation lever; positioning an occlusion clip adjacent to an occlusion site; placing the clip applier in the closed configuration by moving the activation lever from the open configuration to the closed configuration; operating a deployment trigger on the clip applier to release the occlusion clip from the end effector; and/or withdrawing the end effector from the occlusion site, leaving the occlusion clip on the occlusion site.

In a more detailed embodiment of the seventh aspect, applying the external force to the activation lever may include decreasing the amount of external force as the activation lever moves from the closed activation lever configuration to the open activation lever configuration. The method may include, while positioning the occlusion clip adjacent to the occlusion site, maintaining the clip applier in the open configuration by continuing to apply the external force on the activation lever, the force required for maintaining the clip applier in the open configuration being less than the external force required for moving the activation lever from the closed activation lever configuration to the open activation lever configuration. The method may include, before operating the deployment trigger to release the occlusion clip from the end effector, placing the clip applier in an open configuration, repositioning the occlusion clip, and/or placing the clip applier in the closed configuration. Operating the deployment trigger to release the occlusion clip from the end effector may include moving a cable stop relative to an anchoring plate to allow the cable stop to slide by the anchoring plate, thereby allowing proximal movement of a deployment cable affixed to the cable stop. The proximal movement of the deployment cable may release the occlusion clip from the end effector. The method may include, before placing a clip applier in an open configuration, rotating a shaft of the clip applier relative to a handle of the clip applier, the end effector being mounted distally on the shaft and the handle being mounted proximally on the shaft. The method may include, before placing a clip applier in an open configuration, plastically deforming a shaft of the clip applier, the end effector being mounted distally on the shaft and the handle being mounted proximally on the shaft.

It is an eighth aspect of the present disclosure to provide a method of deploying an occlusion clip including placing a clip applier in an open configuration by moving an activation lever of the clip applier from a closed activation lever configuration to an open activation lever configuration; positioning an occlusion clip adjacent to an occlusion site, the occlusion clip being releasably mounted in an end effector of the clip applier; placing the clip applier in a closed configuration by moving the activation lever from the open activation lever configuration to the closed activation lever configuration; operating a deployment trigger on the clip applier to release the occlusion clip from the end effector; and withdrawing the end effector from the occlusion site, leaving the occlusion clip on the occlusion site without puncturing the occlusion site.

In a more detailed embodiment of the eighth aspect, the method may include rotating and deforming a shaft of the clip applier relative to a handle of the clip applier, the clip applier comprising the handle, the shaft selectively rotatably mounted distally on the handle, and the end effector mounted distally on the shaft.

BRIEF DESCRIPTION OF THE DRAWINGS

Example embodiments are described in conjunction with the accompanying drawing figures in which:

FIG. 3 is detailed perspective view of an example occlusion clip being deployed on an anatomical structure;

FIG. 4 is detailed perspective view of an example occlusion clip being deployed on an anatomical structure;

FIG. 5 is detailed perspective view of an example occlusion clip being deployed on an anatomical structure;

FIG. 15 is a detailed perspective view of a distal portion of an example handle;

FIG. 16 is a detailed perspective view of a proximal portion of an example shaft;

FIG. 34 is a perspective view of an example clip applier including a lateral safety tab;

FIG. 35 is a perspective view of an example clip applier including a longitudinal safety tab;

DETAILED DESCRIPTION

Example embodiments according to the present disclosure are described and illustrated below to encompass devices, methods, and techniques relating to surgical procedures. Of course, it will be apparent to those of ordinary skill in the art that the embodiments discussed below are examples and may be reconfigured without departing from the scope and spirit of the present disclosure. It is also to be understood that variations of the example embodiments contemplated by one of ordinary skill in the art shall concurrently comprise part of the instant disclosure. However, for clarity and precision, the example embodiments as discussed below may include optional steps, methods, and features that one of ordinary skill should recognize as not being a requisite to fall within the scope of the present disclosure.

The present disclosure includes, inter alia, medical devices and instruments, and, more specifically, appliers that may be used to apply occlusion devices on anatomical structures. The present disclosure contemplates that, in some circumstances, it may be desirable to occlude an anatomical structure by placing an occlusion device, such as an occlusion clip, on the anatomical structure. For example, in some patients with atrial fibrillation, stagnant blood in the heart's left atrial appendage ("LAA") may be a source of blood clots, which may enter the blood circulation and increase the risk of stroke. In some patients, it may be desirable to occlude the LAA by securely sealing the LAA orifice at the base of the LAA in an effort to reduce this risk without puncturing the LAA.

Figure 1:
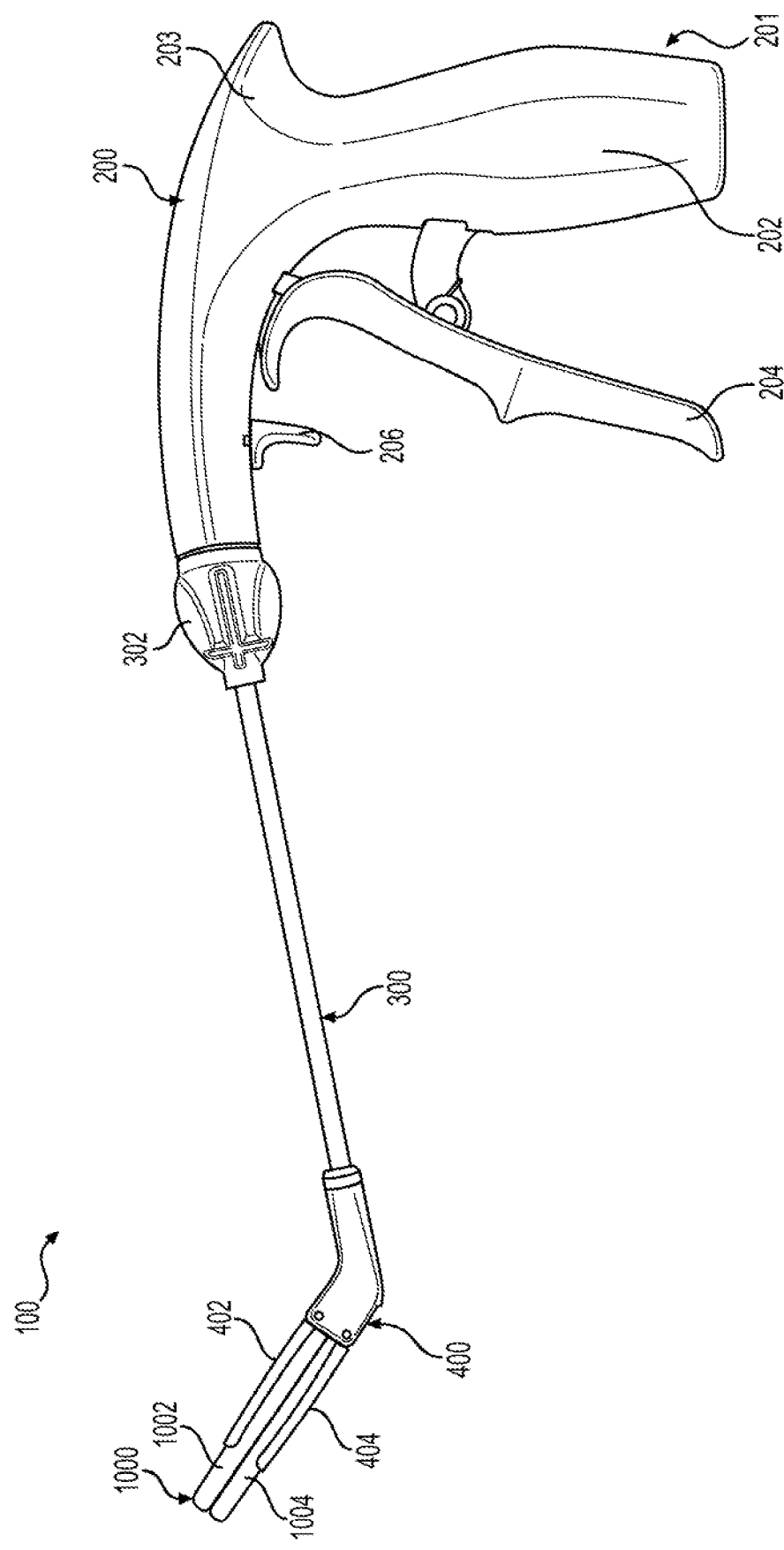
FIG. 1 is a side elevation view of an example clip applier in a closed configuration.
Figure 2:
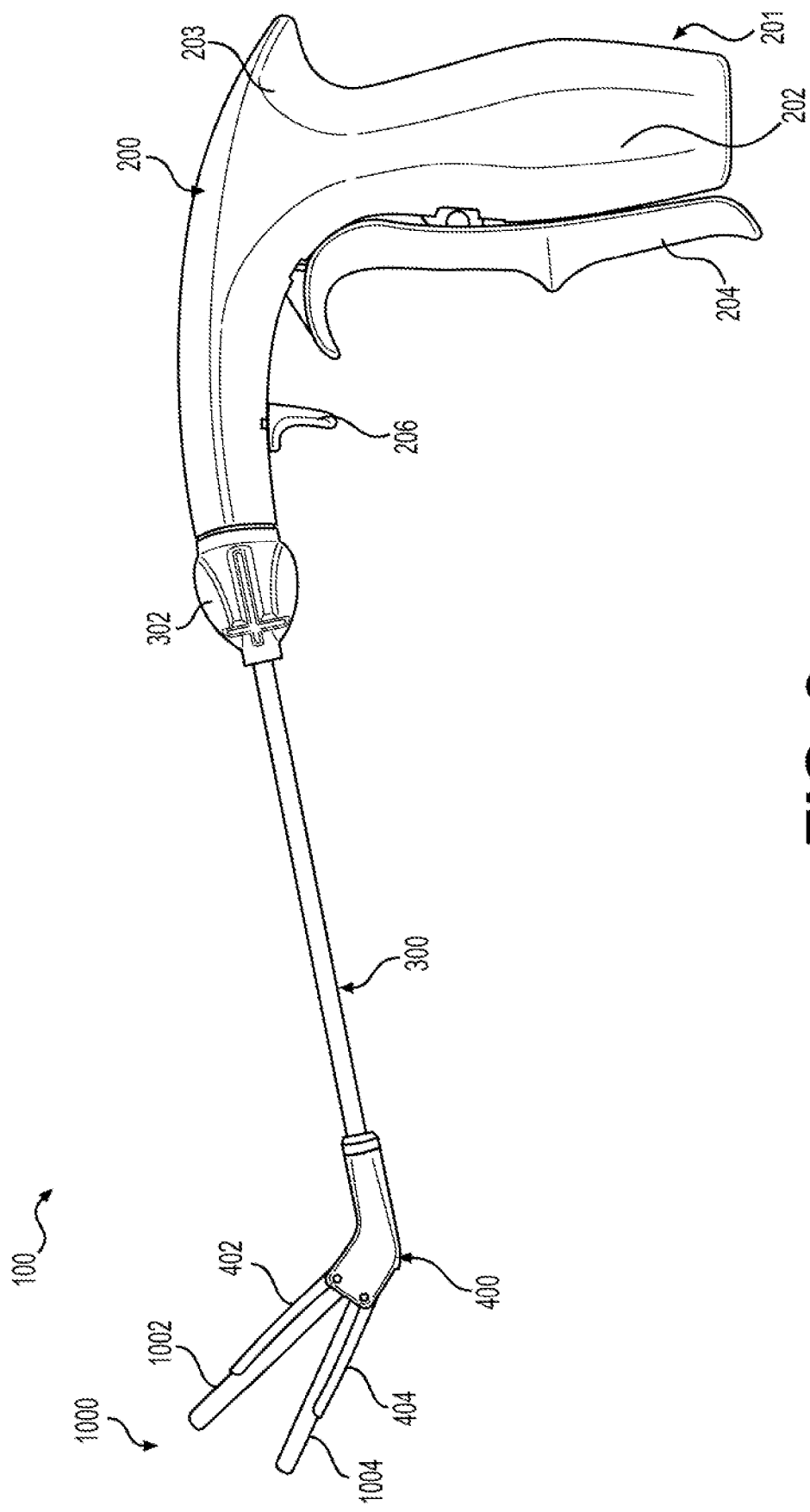
FIG. 2 is a side elevation view of an example clip applier in an open configuration.

FIGS. 1 and 2 are side elevation views of an example clip applier 100 in a closed configuration and an open configuration, respectively, according to at least some aspects of the present disclosure. Clip applier 100 may include a handle 200, a shaft 300 extending generally distally from handle 200, and/or an end effector 400 disposed generally distally on shaft 300. An occlusion clip 1000 may be releasably attached to end effector 400. As used herein, "distal" may refer to a direction generally toward end effector 400 and "proximal" may refer to a direction generally toward handle 200.

In some example embodiments according to at least some aspects of the present disclosure, end effector 400 may include jaws 402, 404, which may be configured to engage respective arms 1002, 1004 of occlusion clip 1000. One or both jaws 402, 404 and respective arms 1002, 1004 may be movable from a closed configuration in which jaws 402, 404 and arms 1002, 1004 are generally parallel (FIG. 1) to an open configuration in which one jaw 402 and its associated arm 1002 is nonparallel relative to the other jaw 404 and its associated arm 1004 (FIG. 2).

In some example embodiments according to at least some aspects of the present disclosure, handle 200 may include a grip 202, which may be generally shaped to be held in a user's hand, such as in a pistol grip fashion. Handle 200 may include an activation lever 204, which may be used to shift clip applier 100 from the closed configuration (FIG. 1) to the open configuration (FIG. 2) and from the open configuration (FIG. 2) to the closed configuration (FIG. 1). For example, when in the closed configuration (FIG. 2), moving activation lever 204 toward grip 202 (generally proximally) may shift clip applier 100 to the open configuration (FIG. 2). When in the open configuration (FIG. 1), moving activation lever 204 away from grip 202 (generally distally) may shift clip applier 100 to the closed configuration (FIG. 1). In some example embodiments, activation lever 204 may be biased away from grip 202, which may place clip applier 100 in the closed configuration (FIG. 1) when external forces, such as from hand grasping of lever 204 and grip 202, are removed from activation lever 204. Portions of handle 200 may be constructed of one or more shells 201, 203.

In some example embodiments according to at least some aspects of the present disclosure, handle 200 may include a deployment trigger 206, which may be used to deploy occlusion clip 1000. For example, moving deployment trigger 206 generally proximally via rotation or sliding motion may release occlusion clip 1000 from end effector 400.

In some example embodiments according to at least some aspects of the present disclosure, the shaft 300 may include a shaft rotation knob 302, which may be operable to selectively allow or prevent rotation of shaft 300 relative to handle 200. For example, moving knob 302 distally (toward end effector 400) may permit rotation of knob 302 and shaft 300 about shaft's 300 longitudinal axis. Moving knob 302 proximally (generally toward grip 202) may prevent rotation of shaft 300 relative to handle 200.

FIGS. 3-5 are detailed perspective views of an occlusion clip 1000 being deployed on an anatomical structure 1100 according to at least some aspects of the present disclosure. Referring to FIGS. 1-5, some example clip appliers 100 according to at least some aspects of the present disclosure may be used as follows. Clip applier 100, with occlusion clip 1000 attached, may be placed in an open configuration by operating activation lever 204 and positioned to locate occlusion clip 1000 adjacent an occlusion site 1102 on an anatomical structure 1100 (FIGS. 2 and 3). Clip applier 100 may be placed into the closed configuration by operating activation lever 204, and the positioning of occlusion clip 1000 at the occlusion site 1102 of the anatomical structure 1100 may be verified (FIGS. 1 and 4). If necessary, clip applier 100 may be returned to the open configuration by operating activation lever 204 (FIGS. 2 and 3), repositioned, and returned to the closed configuration by operating activation lever 204 (FIGS. 1 and 4). Deployment trigger 206 (FIGS. 1 and 2) may be operated to deploy occlusion clip 1000, which may release occlusion clip 1000 from end effector 400. Clip applier 100 may be moved to withdraw end effector 400 from the anatomical structure 1100, leaving occlusion clip 1000 on occlusion site 1102 of the anatomical structure 1100 (FIG. 5). Occlusion clip 1000 may remain as a permanent implant on anatomical structure 1100. In some example embodiments according to at least some aspects of the present disclosure, anatomical structure 1100 may be occluded by clip 1000 without being punctured.

The present disclosure contemplates that some occlusion device applicators may require one hand to hold the applicator and another hand to release the occlusion device from the applicator. For example, the present disclosure contemplates that some occlusion device applicators may utilize an occlusion clip release mechanism that requires manual cutting (e.g., with a scalpel) of sutures attaching the occlusion clip to the applicator. The present disclosure contemplates that, in some circumstances, it may be advantageous to avoid utilizing a sharp instrument, such as a scalpel or scissors, near a patient's heart or a surgeon's hand. The present disclosure contemplates that some occlusion device applicators may require a user to pull deployment cables away from the applicator to deploy the occlusion device. The present disclosure contemplates that, in some circumstances, it may be advantageous to avoid relatively large movements.

The present disclosure contemplates that, in some circumstances, it may be desirable to provide an occlusion device applicator that may be both held and operated by one hand. For example, during some LAA occlusion procedures, a surgeon's left hand may be used to support the patient's heart while the surgeon's right hand may be used to hold, position, and/or actuate the occlusion device applicator.

Some example clip appliers 100 according to at least some aspects of the present disclosure may be configured to permit one-handed operation. Some example clip appliers 100 may be held in one hand, shifted between the open and closed configurations by the holding hand, and/or actuated to deploy occlusion clip 1000 by the holding hand. For example, some clip appliers 100 according to at least some aspects of the present disclosure may be configured for operation of activation lever 204 by one or more fingers of the holding hand. Some example clip appliers 100 according to at least some aspects of the present disclosure may be configured for operation of deployment trigger 206 by one finger, such as the holding hand's index finger.

Figure 6:
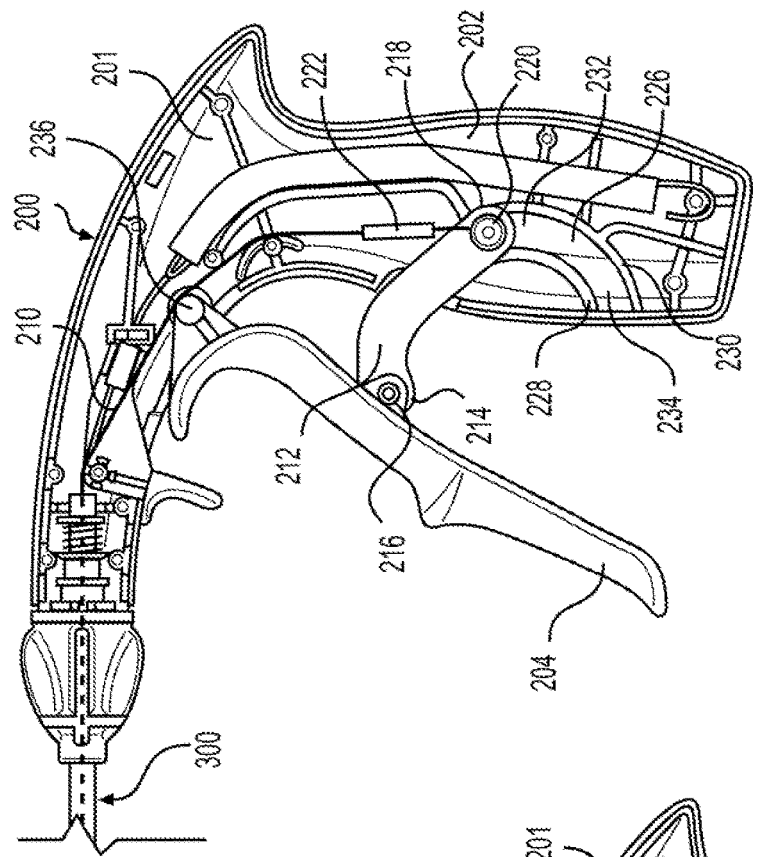
FIG. 6 is an interior side elevation view of an example handle in a closed configuration.
Figure 7:
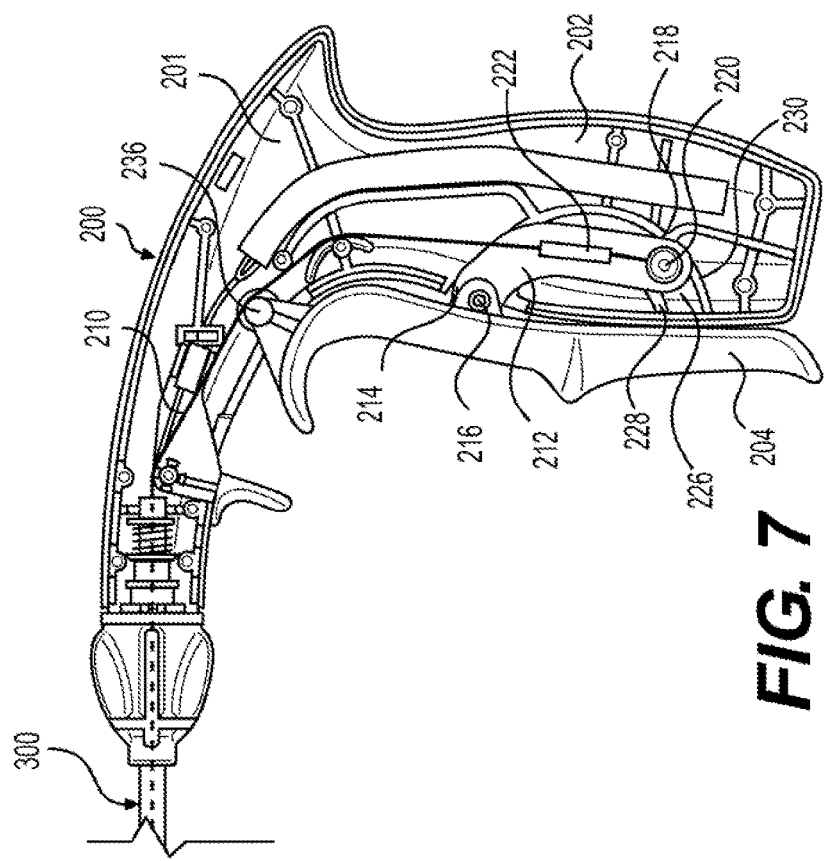
FIG. 7 is an interior side elevation view of an example handle in an open configuration.
Figure 8:
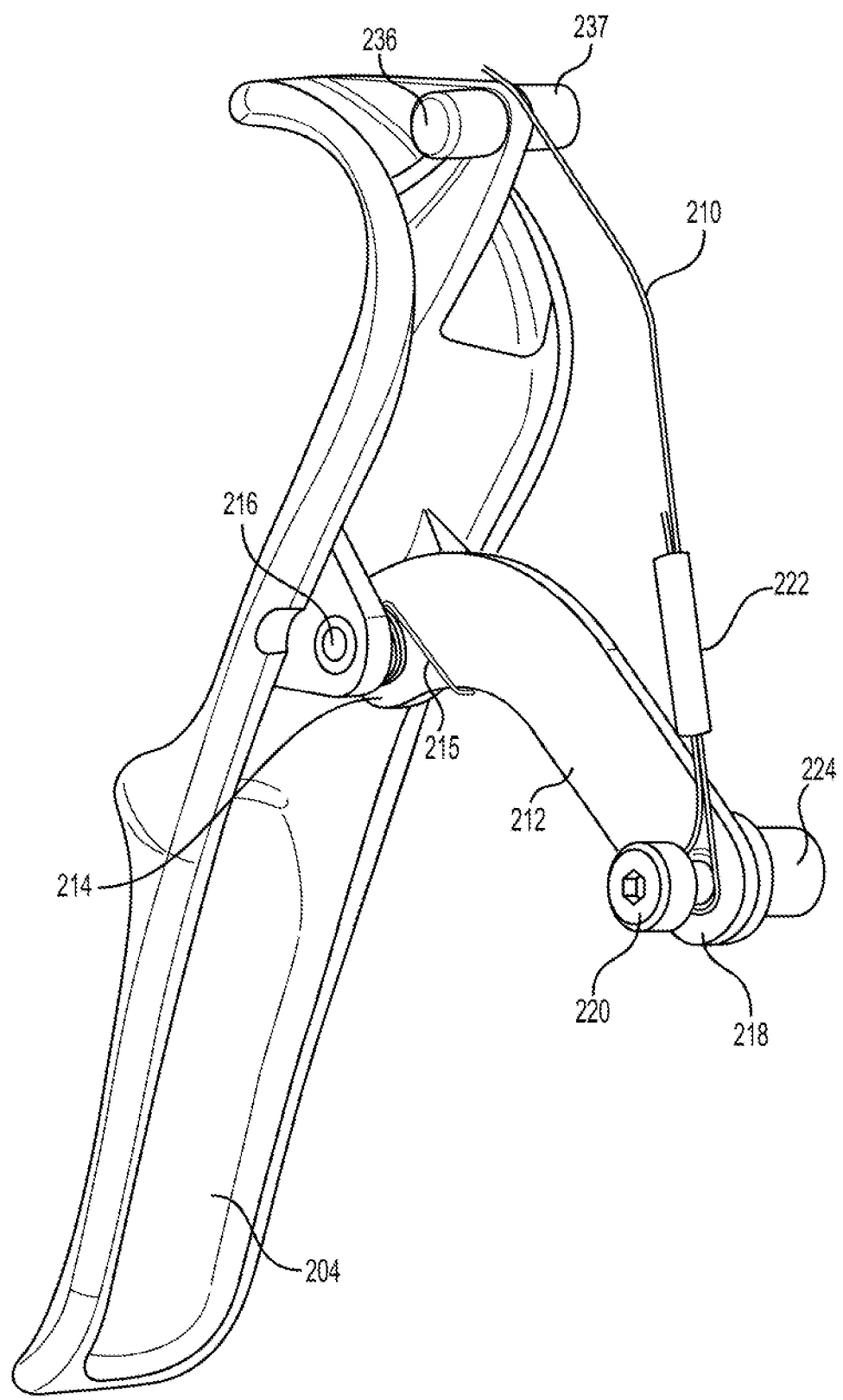
FIG. 8 is a perspective view of an example activation lever mechanism.
Figure 36:
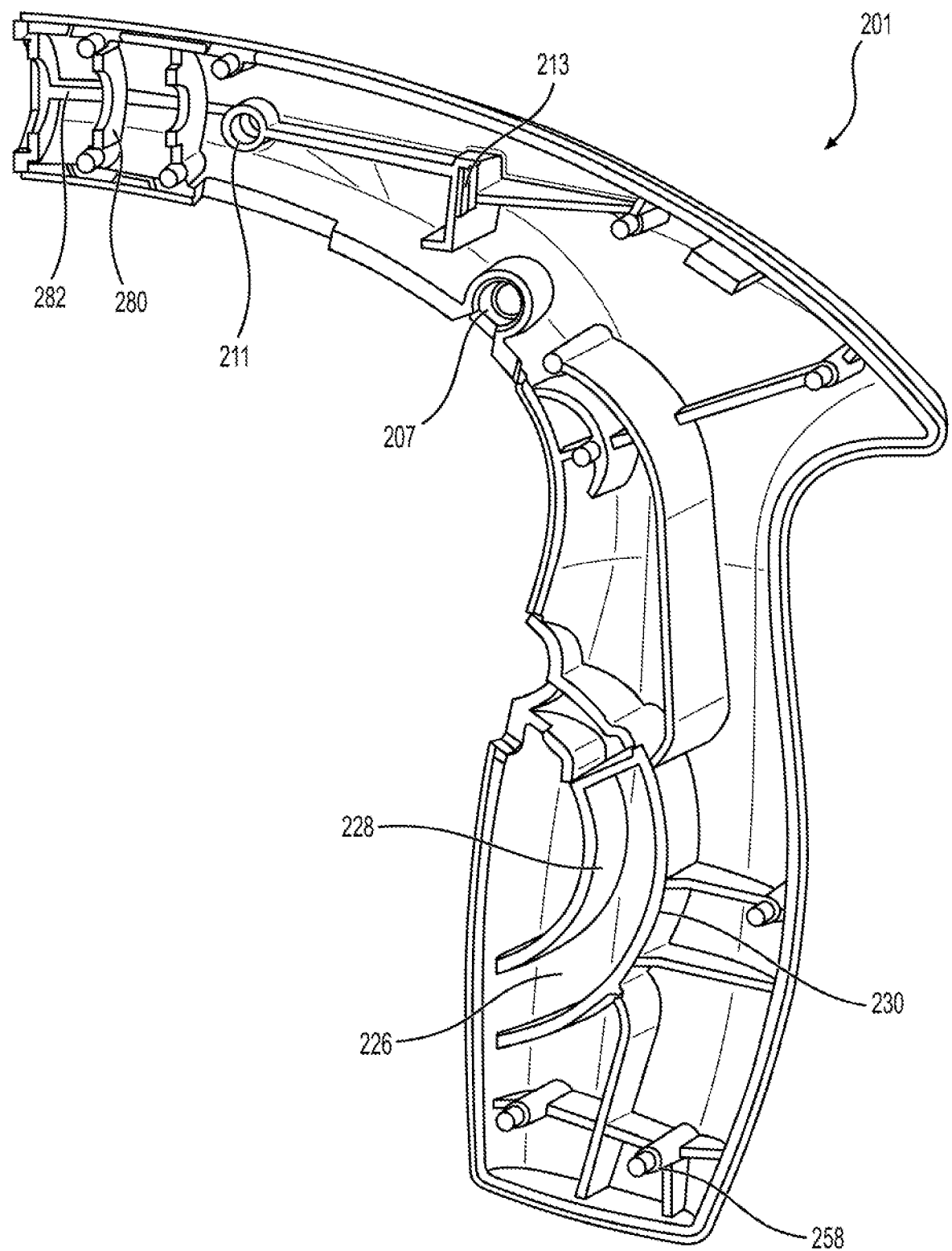
FIG. 36 is an interior perspective view of an example shell of a handle.

FIGS. 6 and 7 are interior side elevation views of an example handle 200 in a closed configuration and an open configuration, respectively, according to at least some aspects of the present disclosure. FIG. 8 is a perspective view of an example activation lever 204 mechanism, according to at least some aspects of the present disclosure. In some example embodiments, activation lever 204 may be mounted to rotate about activation lever pivot journals 236, 237. For example, activation lever pivot journal 236 may rotatably engage a bearing 205 disposed on shell 203 of handle 200 (FIG. 37) and a pivot journal 237 may rotatably engage a bearing 207 disposed on shell 201 of handle 200 (FIG. 36). Activation lever 204 may be operatively coupled to jaws 402, 404 of end effector 400 (FIGS. 1 and 2) by an activation cable 210. Activation cable 210 may extend through the interior of handle 200 and through a hollow channel extending through shaft 300 to end effector 400 (FIGS. 1 and 2).

Referring to FIGS. 6-8, in some example embodiments, activation lever 204 may be operatively coupled to activation cable 210 by a linkage 212. A first end 214 of linkage 212 may be pivotably attached to activation lever 204, such as by a rivet 216. In some example embodiments, a torsion spring 215 may be mounted to activation lever 204 and linkage 212 near rivet 216 such that linkage 212 is torsionally biased to rotate towards activation lever pivot journal 236, which may bias activation lever 204 toward the open configuration (FIGS. 1 and 6). A second end 218 of linkage 212 may be attached to activation cable 210, such as by looping activation cable 210 around a fastener 220 (e.g., a screw) extending through linkage 212 and installing a crimp tube 222 on activation cable 210. In some example embodiments, a track follower 224 (e.g., a bushing) may be affixed to second end 218 of linkage 212, such as by fastener 220.

In some example embodiments, track follower 224 may be slidably disposed along a track 226 within handle 200. Track 226 may be formed by a first sidewall 228 spaced apart from a second sidewall 230 to slidably receive track follower 224 therebetween. In some example embodiments, first sidewall 228 and/or second sidewall 230 may be formed as part of handle 200 shell 201. First sidewall 228 and second sidewall 230 may define track 226 in a nonlinear shape, such as a generally curved, arcuate shape.

In some example embodiments, moving activation lever 204 from the closed configuration (FIG. 6) to the open configuration (FIG. 7), such as by a user applying a generally proximal force to activation handle (such as by squeezing activation handle 204 towards grip 202 with the fingers), may cause track follower 224 to move within track 226 from a first location 232 to a second location 234. Such movement may pull activation cable 210 generally proximally (e.g., generally away from end effector 400) through shaft 300. Such proximal movement of activation cable 210 may cause jaws 402, 404 of end effector 400 to move from the closed configuration (FIG. 1) to the open configuration (FIG. 2). Reducing and/or removing the user-applied proximal force applied to activation handle 204 may allow activation handle 204, track follower 224, and activation cable 210 to return to the closed configuration, such as by the action of torsion spring 215 and/or a closed-biased occlusion clip 1000.

The present disclosure contemplates that some occlusion device applicators may utilize a mechanical lock and/or a sustained user-applied force to hold an occlusion device (e.g., an occlusion clip) open while positioning the occlusion device on an anatomical structure, such as a LAA. The present disclosure contemplates that while a mechanical lock may effectively hold the occlusion device open during positioning, such a mechanism may require a cumbersome unlocking action (e.g., disengaging an inconveniently located lock) to permit closure and/or deployment of the occlusion device. For example, on some devices, it may be necessary for a user to visually locate the lock so that it may be activated and/or deactivated. The present disclosure contemplates that some occlusion device applicators relying on sustained user-applied force to keep the occlusion device open may avoid some of the disadvantages of mechanical locks; however, the user may experience disadvantages such as fatigue and/or compromised dexterity if the required force is high.

Referring to FIGS. 6-8, as will be apparent to one of skill in the art, the length of linkage 212 between rivet 216 and track follower 224, the length of activation lever 204 between activation lever pivot journal 236 and rivet 216, and/or the location and/or shape of track 226 between first location 232 and second location 234 may affect the force that must be applied by a user over the travel of activation lever 204. In some example embodiments, it may be desirable to limit the cam angle to maintain smooth operation, particularly in portions of travel of activation lever 204 where forces are higher. For example, the curvature of track 226 may be limited to cause a generally straighter motion of track follower 224 in portions of travel of activation lever 204 where forces are higher. As will be apparent to one of skill in the art, varying the configuration of these various components may vary the force and distance output of the mechanism as activation lever 204 travels between the open configuration and closed configuration.

Some example embodiments according to at least some aspects of the present disclosure may be configured to require less user-applied force on activation lever 204 near the end of its travel, such as when clip applier is near and/or in the open configuration. For example, the pivot point of activation lever 204 (activation lever pivot journal 236), the direction of activation cable 210 generally between fastener 220 and activation lever pivot journal 236, and track follower 224 may be nearly aligned as activation lever 204 approaches the open configuration, which may increase the mechanical advantage and/or reduce the required force on activation lever 204.

In some example embodiments according to at least some aspects of the present disclosure, a clip applier 100 may be configured to utilize a user-applied hold-open force to maintain the open configuration (FIG. 2) that is less than the force required to shift to the open configuration (FIG. 2) from the closed configuration (FIG. 1). Some example clip appliers 100 may require application of a generally constant force to activation lever 204 to shift from the open configuration (FIG. 1) toward the closed configuration (FIG. 2) for a substantial portion (e.g., for about 85%) of the length of travel of activation lever 204. Then, for the travel remaining (e.g., about 15%), the force required to continue to the open configuration (FIG. 2), and/or the force required to hold activation lever 204 in the open configuration (FIG. 2), may be less than about half of the force required to begin the shift from closed configuration (FIG. 1) to the open configuration (FIG. 2).

In some example embodiments, activation lever 204 may reach a hard stop when clip applier 100 is in the fully open configuration (FIG. 2), which may indicate to the user that clip applier 100 is in the open configuration (FIG. 2) and/or that no additional force or travel may be required. For example, as shown in FIGS. 2 and 7, a proximal surface of activation lever 204 may contact a distal surface of grip 202.

Figure 20:
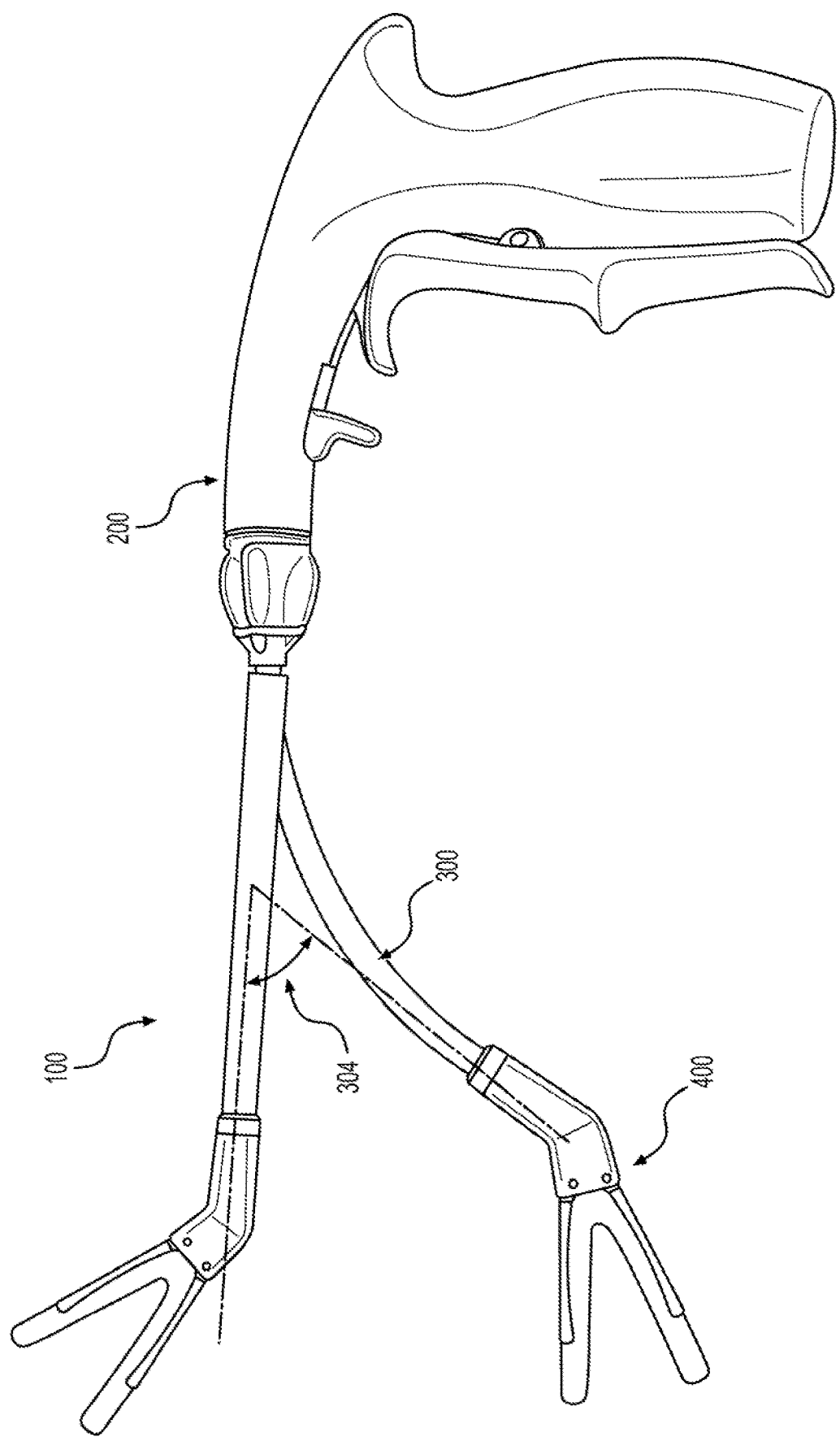
FIG. 20 is a side elevation view of an example clip applier with a shaft in a bent configuration.

In some example embodiments, an activation mechanism may include a locking feature, which may be configured to hold clip applier 100 in the open configuration (FIG. 20). For example, a lock similar to that described in described in U.S. Patent Application Publication No. 2017/0014135, published Jan. 19, 2017, which is incorporated by reference, may be utilized.

Figure 9:
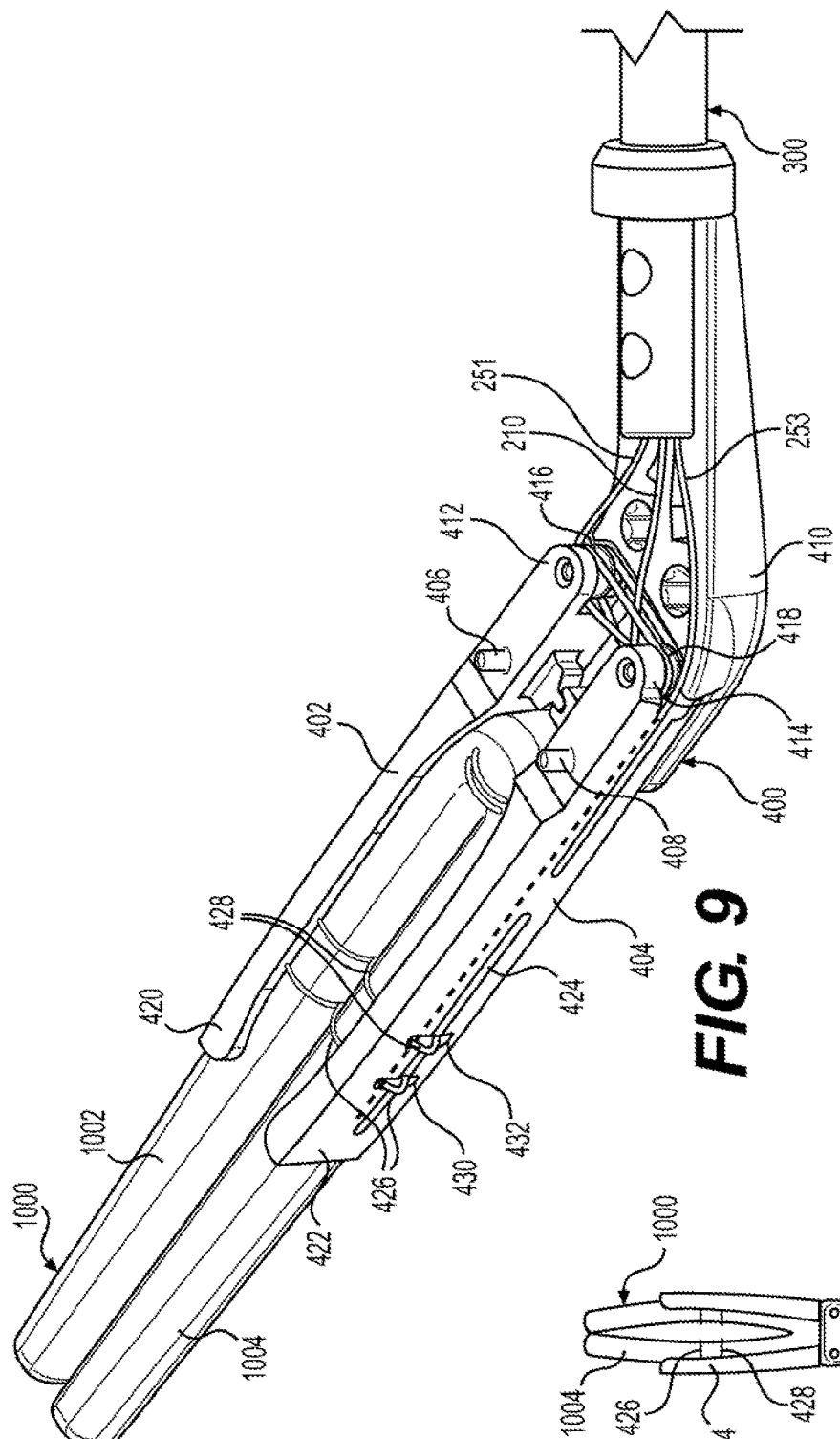
FIG. 9 is a detailed interior perspective view of an example end effector.
Figure 10:
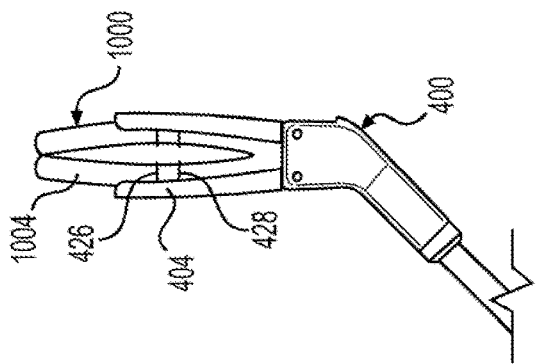
FIG. 10 is a side elevation view of an example end effector showing tip-first closure of an occlusion clip.

FIG. 9 is a detailed interior perspective view of an example end effector 400 and FIG. 10 is a side elevation view of an example end effector 400 showing tip-first closure of an example occlusion clip 1000, according to at least some aspects of the present disclosure. In some example embodiments, jaws 402, 404 and respective arms 1002, 1004 of occlusion clip 1000 (prior to deployment) may be shifted between the closed configuration (FIG. 1) and the open configuration (FIG. 2) by the retraction (e.g., pulling in a proximal direction) or extension (e.g., allowing movement in a distal direction) of activation cable 210, which may be effected by operation of activation handle 204 (FIGS. 6 and 7).

In some example embodiments according to at least some aspects of the present disclosure, jaw 402 may be pivotably mounted to a pivot pin 406, and jaw 404 may be pivotably mounted to a pivot pin 408. Pivot pins 406, 408 may be affixed to end effector 400 housing 410. End effector 400 housing 410 may include two mirror-image portions, one of which is not shown in FIG. 9 for clarity. Activation cable 210 may extend distally from handle 200 (FIGS. 6 and 7), through shaft 300, and to a double-tackle pulley mechanism operatively disposed on the proximal portions 412, 414 of jaws 402, 404, respectively. Proximal movement of activation cable 210, such as by movement of activation lever 204 from the closed configuration to the open configuration (FIGS. 6 and 7), may cause the length of the activation cable 210 extending between pulleys 416, 418 to decrease, thereby causing proximal ends 412, 414 of jaws 402, 404 to move toward one another. This movement of proximal ends 412, 414 of jaws 402, 404 toward one another may coincide with distal ends 420, 422, respectively, of jaws 402, 404 pivoting away from one another about to effectively open jaws 402, 404 and correspondingly opening occlusion clip 1000. Distal movement of activation cable 210, such as by movement of activation lever 204 from the open configuration to the closed configuration (FIGS. 6 and 7), may cause the length of the activation cable 210 extending between pulleys 416, 418 to increase (such as by action of torsion spring 215 (FIG. 8) and/or a closed-biased occlusion clip 1000), thereby allowing proximal ends 412, 414 of jaws 402, 404 to move away from one another. This movement of proximal ends 412, 414 of jaws 402, 404 apart may coincide with distal ends 420, 422, respectively, of jaws 402, 404 pivoting towards one another about to effectively close jaws 402, 404 and correspondingly closing occlusion clip 1000.

Referring to FIG. 10, arm 1004 of occlusion clip 1000 may be attached to jaw 404, such as by sutures 426, 428, which may be disposed proximally with respect to the center of the length of arm 1004 to cause the distal tips of occlusion clip 1000 close first when clip applier 100 (FIGS. 1 and 2) is shifted from the open configuration (FIG. 2) to the closed configuration (FIG. 1).

U.S. Published Patent Application No. 2018/0036007, published Feb. 8, 2018, and which is incorporated by reference, provides further details regarding the construction and operation of end effectors 400 that may be operated by an activation cable 210 ("control wire") that may be fed around pulleys and utilized to cause jaws 402, 404 to pivot for opening and closing.

It is within the scope of the present disclosure to utilize alternative jaw opening mechanisms as known in the art, such as cams, gears, and/or linkages, in connection with example embodiments according to at least some aspects of the present disclosure. It is within the scope of the present disclosure utilize jaw opening mechanisms described in U.S. Patent Application Publication No. 2017/0014135, published Jan. 19, 2017, which is incorporated by reference.

Figure 11:
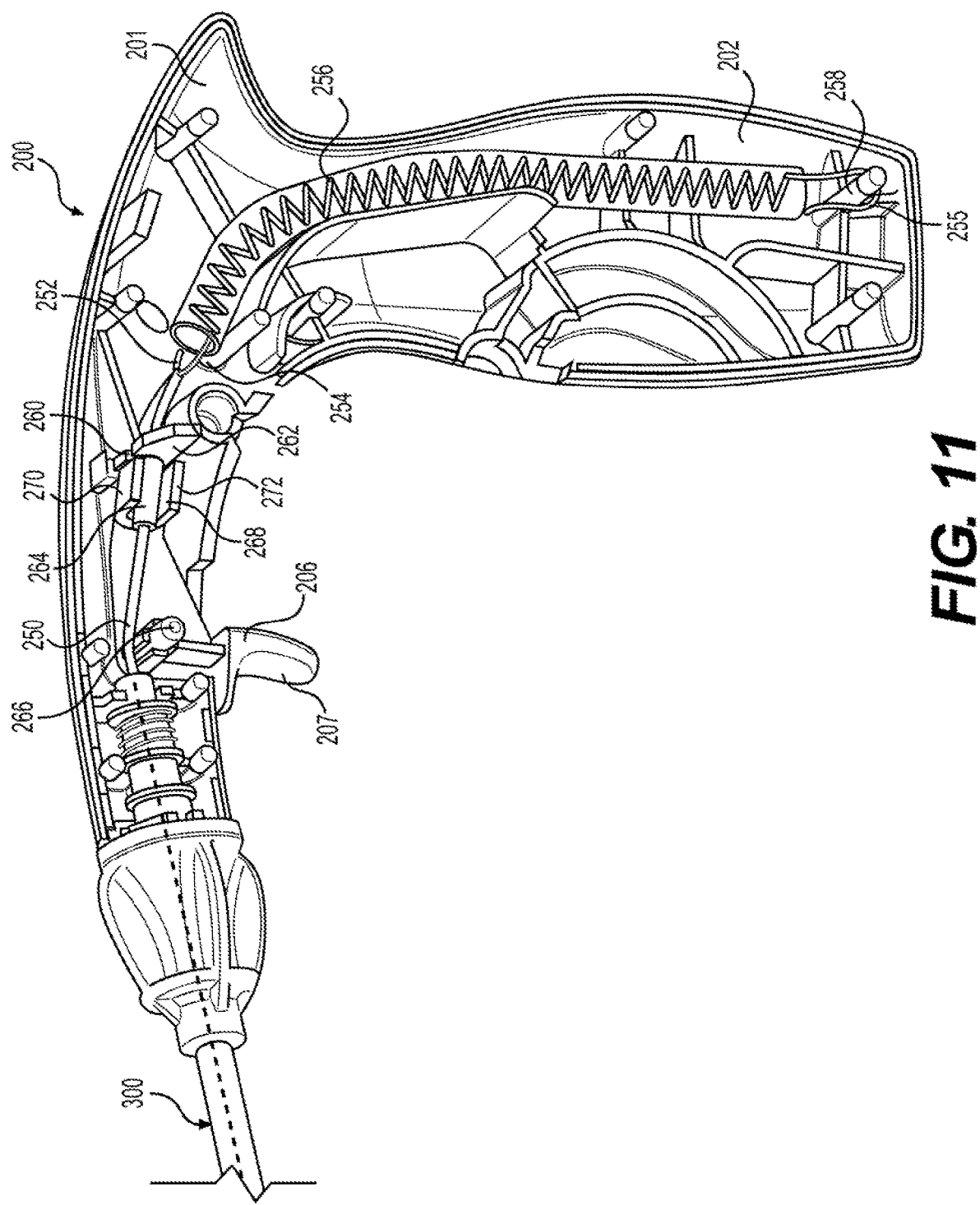
FIG. 11 is an interior perspective view of an example clip applier handle showing occlusion clip release components in a before deployment configuration.
Figure 12:
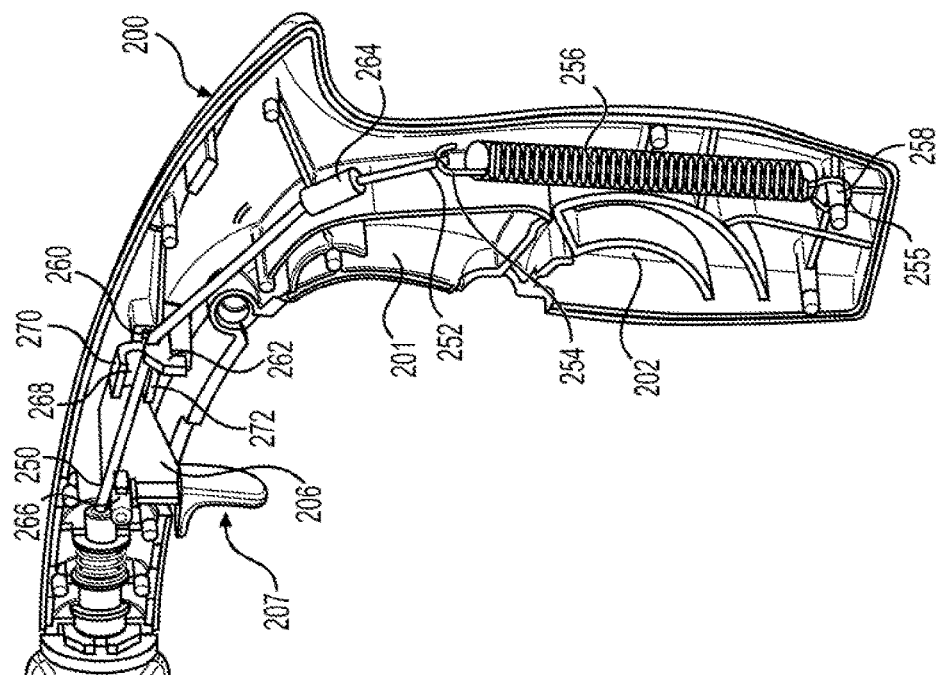
FIG. 12 is an interior perspective view of an example clip applier handle showing occlusion clip release components in a during deployment configuration.
Figure 13:
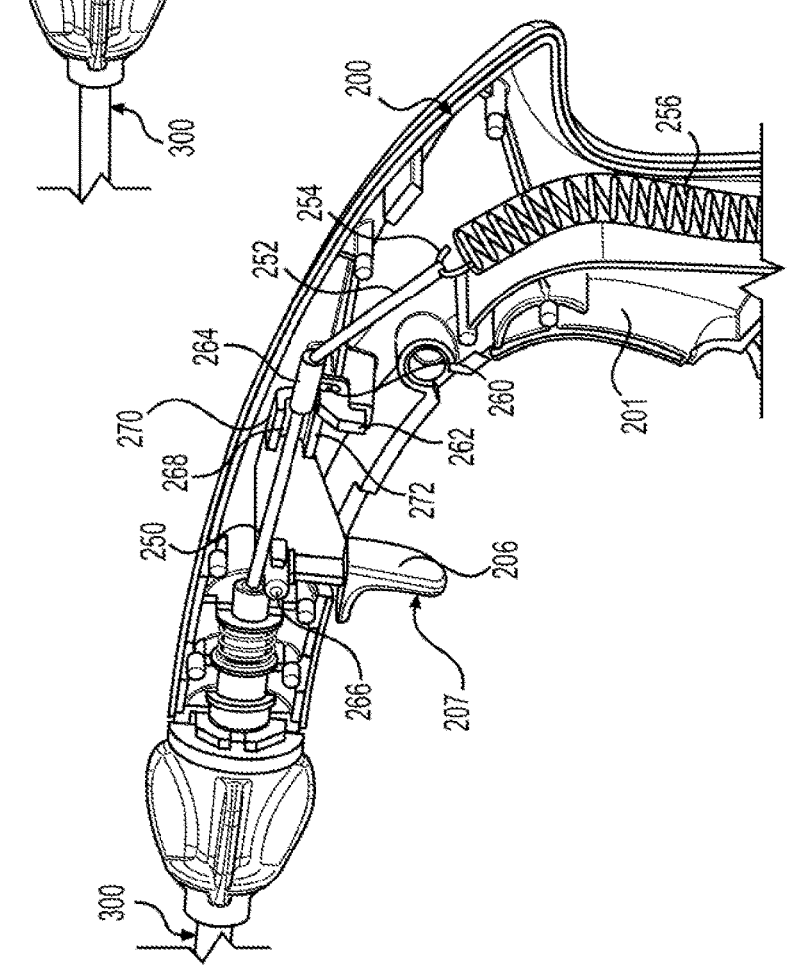
FIG. 13 is an interior perspective view of an example clip applier handle showing occlusion clip release components in an after deployment configuration.
Figure 37:
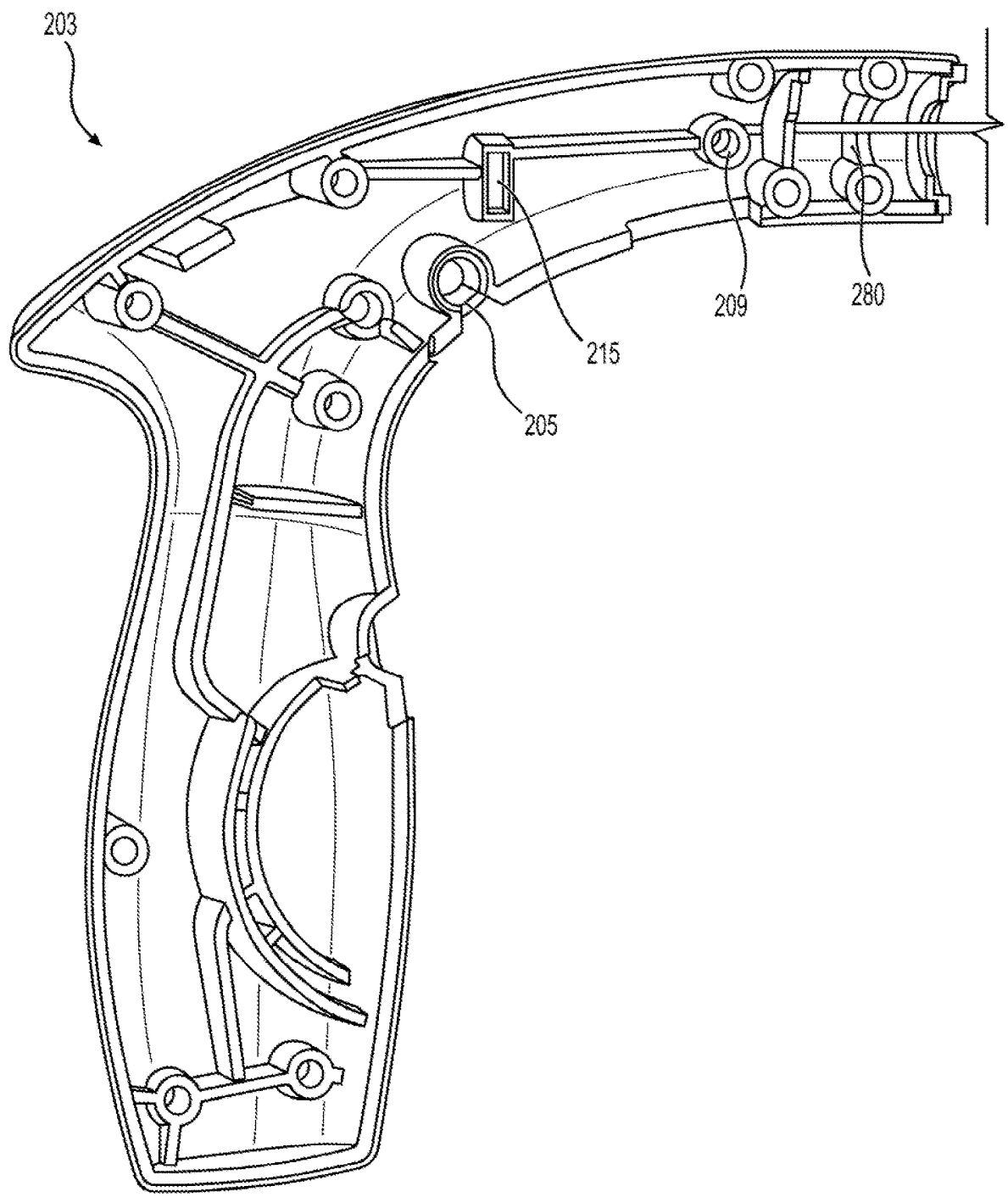
FIG. 37 is an interior perspective view of an example shell of a handle; all in accordance with at least some aspects of the present disclosure.

FIGS. 11-13 are interior perspective views of an example handle 200 showing occlusion clip release components in before deployment, during deployment, and after deployment configurations, respectively, all according to at least some aspects of the present disclosure. Deployment trigger 206 may be actuated by a user pressing generally proximally on a trigger face 207. Deployment trigger 206 may be operatively coupled to jaws 402, 404 of end effector 400 (FIGS. 1 and 2) by a deployment cable 250, which may extend from handle 200 to end effector 400 through a hollow channel extending through shaft 300. A proximal end 252 of deployment cable 250 may be coupled to a first end 254 of an elastic member, such as an extension spring 256. A second end 255 of extension spring 256 may be affixed to the interior of handle 200, such as at a boss 258 formed in shell 201. Deployment cable 250 may extend from first end 254 of extension spring 256, through a slot 260 in an anchoring plate 262, and to a cable stop, such as a crimp sleeve 264. Anchoring plate 262 may be fixedly mounted to shells 201, 203 by extending into anchoring plate slots 213, 215, respectively (FIGS. 36 and 37). Slot 260 in anchoring plate 262 may be wider than deployment cable 250 and narrower than crimp sleeve 264, thereby allowing deployment cable 250 to pass through slot 260 while preventing crimp sleeve 264 from passing through slot 260. Crimp sleeve 264 may be fixedly attached to deployment cable 250, which may form a loop at proximal end 252 of deployment cable 250. Deployment cable 250 may extend distally from the crimp sleeve 264 through shaft 300 to end effector 400 (FIGS. 1 and 2).

In some example embodiments, deployment trigger 206 may be configured to pivot with respect to handle shells 201, 203, such as by a deployment trigger pivot journal 266 pivotably engaging a bearing 209 disposed on shell 203 of handle 200 (FIG. 37) and a second deployment trigger pivot journal (not shown) engaging a bearing 211 disposed on shell 201 of handle 200 (FIG. 36). Deployment trigger 206 may include a slot 268 configured to slidably receive crimp sleeve 264 of deployment cable 250. For example, slot 268 may be at least partially defined by a first wall 270 and a second wall 272 spaced apart to accept crimp sleeve 264 therebetween.

Referring to FIG. 11, which illustrates an example before deployment configuration according to at least some aspects of the present disclosure, deployment trigger 206 may be positioned in a pre-deployment configuration with slot 268 of deployment trigger 206 generally aligned with slot 260 of anchoring plate 262. Extension spring 256 may be substantially extended and may apply a pulling force on proximal end 252 of deployment cable 250. A proximal end of crimp sleeve 264 (which may be fixedly attached to deployment cable 250 at a fixed position) may at least partially abut a distal surface of anchoring plate 262. Because crimp sleeve 264 may be unable to pass through slot 260 in anchoring plate 262, extension spring 256 may be held in its extended configuration. In the before deployment configuration, deployment trigger 206 may be actuated by a user pressing generally proximally on trigger face 207, such as by a pulling or squeezing motion of the user's index finger.

Referring to FIG. 12, which illustrates an example during deployment configuration according to at least some aspects of the present disclosure, deployment trigger 206 may be rotated from the before deployment configuration (FIG. 11) to a deployment configuration in which slot 268 of deployment trigger 206 is aligned generally adjacent to anchoring plate 262. In some example embodiments, rotating deployment trigger 206 to the deployment configuration may move crimp sleeve 264 relative to anchoring plate 262. With slot 268 of deployment trigger 206 aligned generally adjacent to anchoring plate 262, crimp sleeve 264 may no longer be restrained by anchoring plate 262. The tensile force exerted by extension spring 256 on deployment cable 250 may cause crimp sleeve 264 to slide generally proximally from within slot 268 of deployment trigger 206 by anchoring plate 262.

Referring to FIG. 13, which illustrates an example after deployment configuration according to at least some aspects of the present disclosure, extension spring 256 may be in a relaxed configuration and/or deployment cable 250 may be retracted proximally to a position in which crimp sleeve 264 has cleared anchoring plate 262. Deployment cable 250 may extend through slot 260 in anchoring plate 262 and/or through slot 268 in deployment trigger 206. In some example embodiments, deployment cable 250 may be retracted by the force of extension spring 256 about 5 cm (about 2 inches). Compare the position of crimp sleeve 264 in FIG. 11 and FIG. 13, for example.

Referring to FIGS. 11-13, in some example embodiments, deployment trigger 206, anchoring plate 262, and related components may be configured to reduce the likelihood of unintentional actuation, such as due to handling of the device. For example, deployment trigger 206 may be located on handle 200 where it may be unlikely to be inadvertently actuated, deployment trigger 206 may be protected, such as by a trigger guard (see, e.g., FIG. 26), actuation of deployment trigger 206 may require removal or disabling a safety device (see, e.g., FIGS. 34 and 35), and/or the force and/or travel required actuate deployment trigger 206 may reduce the likelihood of unintentional actuation.

In some example embodiments, the amount of tensile force exerted on deployment cable 250 by spring 256 and/or the angle at which the proximal end of crimp sleeve 264 contacts the distal face of anchoring plate 262 may affect the force that must be applied to trigger face 207 to shift deployment trigger 206 to cause crimp sleeve 264 to clear anchoring plate 262. As another example, the depth of slot 260 in anchoring plate 262 and/or the angle of pull of deployment cable 250 on the proximal side of anchoring plate 262 may affect the distance that slot 268 of deployment trigger 206 must move to cause crimp sleeve 264 to clear anchoring plate 262. Similarly, the relative lengths of deployment trigger 206 between each of trigger face 207 and slot 268 and the pivot point of deployment trigger 206 (e.g., trigger pivot journal 266) may affect the distance that trigger face 207 must be moved by a user to cause crimp sleeve 264 to clear anchoring plate 262, as well as the force that must be applied to trigger face 207. In some example embodiments, deployment trigger 206, anchoring plate 262, and related components may be configured to require a force of about two and about ten pounds on trigger face 207 and/or a distance of travel of trigger face 207 of about 0.5 cm (about 0.2 inches).

Some example embodiments according to at least some aspects of the present disclosure may provide tactile and/or audible indications that deployment trigger 206 and related components have been successfully actuated, thus releasing occlusion clip 1000 from end effector 400. In some example embodiments, inertia from extension spring 256 hitting its stop location may provide tactile and/or audible indications that the deployment mechanism has been actuated. Some example embodiments may include a noise-producing component, such as a bell.

It is within the scope of the present disclosure to utilize elastic members other than extension springs, such as elastomers (e.g., silicon, rubber, latex, neoprene, and/or polyurethane). Some example embodiments may utilize alternative springs, such as compression springs, leaf springs, and/or constant force springs, for example.

Figure 14:
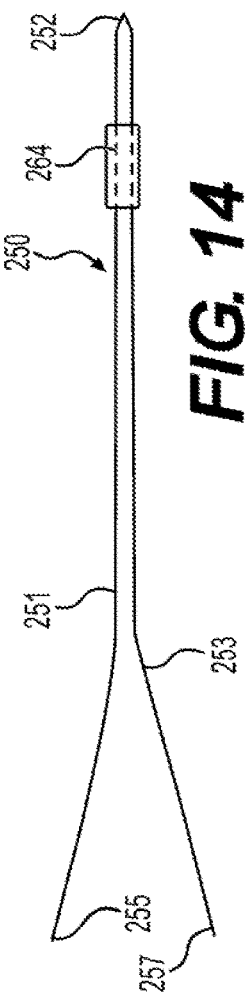
FIG. 14 is an elevation view of an example deployment cable.

FIG. 14 is an elevation view of an example deployment cable 250 according to at least some aspects of the present disclosure. Deployment cable 250 may include a first strand 251 and/or a second strand 253 extending distally from crimp sleeve 264. In some example embodiments, deployment cable 250 may be constructed from a length of cable bent near its center to form a loop at proximal end 252 for attachment to extension spring 256 (FIGS. 11-13). First strand 251 may extend through shaft 300 to jaw 402, ending at a first strand end 255. Second strand 253 may extend through shaft 300 to jaw 404, ending at a second strand end 257. In some example deployment cables 250 including first strand 251 and second strand 253, pulling on proximal end 252 (such as by extension spring 256 (FIGS. 11-13)) may cause first strand end 255 and second strand end 257 to move proximally generally in parallel.

Referring to FIG. 9, a detailed interior perspective view of an example end effector 400 according to at least some aspects of the present disclosure, first strand 251 and second strand 253 of deployment cable 250 may extend distally from handle 200, through shaft 300, to end effector 400. The following description focuses on jaw 404 and second strand 253; however, jaw 402 and first strand 251 may be configured and operate in a substantially similar manner.

In some example embodiments, second strand 253 of deployment cable 250 may extend distally within jaw 404 within a channel 424. One or more of suture loops 426, 428 (e.g., retainer loops) may be longitudinally spaced apart, may extend around arm 1004 of occlusion clip 1000, and/or may extend through respective openings 430, 432 through jaw 404. Second strand 253 of deployment cable 250 may extend longitudinally through each suture loop 426, 428. In this fashion, arm 1004 of occlusion clip 1000 may be inhibited from detaching from jaw 404 until second strand 253 is withdrawn from suture loops 426, 428 (e.g., retracted proximally).

In some example embodiments, to release occlusion clip 1000 from end effector 400, deployment cable 250 is repositioned proximally (such as by actuating deployment trigger 206 to allow extension spring 256 to withdraw cable 250 proximally) and second strand 253 discontinues engagement with the suture loops 426, 428 that were previously concurrently attached to occlusion clip 1000 and jaw 404. When the engagement between strand 253 and the suture loops 426, 428 is discontinued, suture loops 426, 428 may be pulled through respective openings 430, 432 toward arm 1004 to free arm 1004 of occlusion clip 1000 from jaw 404.

U.S. Published Patent Application No. 2018/0036007, published Feb. 8, 2018 and which is incorporated by reference, provides further details regarding the construction and operation of end effectors 400 holding occlusion clips 1000 that may be released by withdrawing deployment cables 250 ("deployment wire") from suture loops 426, 428.

In some example embodiments, alternatives to suture loops 426, 428 and deployment cable 250 may be utilized to releasably retain occlusion clip 1000 in jaws 402, 404. For example, slip knots, interference fits, suture cutting, and/or pull cords may be used.

The present disclosure contemplates that some occlusion device applicators may be provided with an end effector that is fixed (e.g., not rotatable) with respect to the handle. As a result, rotating the end effector (and attached occlusion clip) requires the user to rotate the handle. The present disclosure contemplates that providing an occlusion device applicator with a rotatable shaft may provide ergonomic advantages for the user and/or may better accommodate both left-handed and right-handed use. Additionally, the present disclosure contemplates that an occlusion device applicator with a rotatable shaft may reduce the difficulty of accessing the desired occlusion site, particularly in connection with anatomical structures that may vary in location and/or orientation from patient to patient. Further, the present disclosure contemplates that providing an occlusion device applicator with a rotatable shaft may allow the device to be packaged in a smaller configuration than the configuration in which it may be used. The present disclosure contemplates that a smaller packaging configuration may be advantageous for shipping, storage, and/or sterilization, for example.

Figure 17:
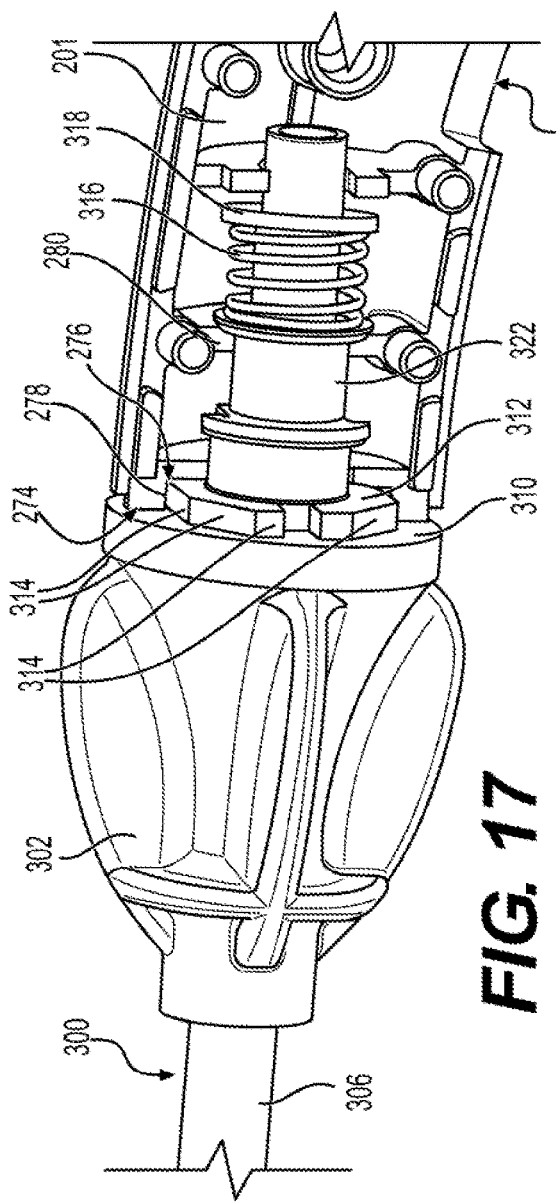
FIG. 17 is a detailed internal perspective view of an example shaft and handle in a locked configuration.
Figure 18:
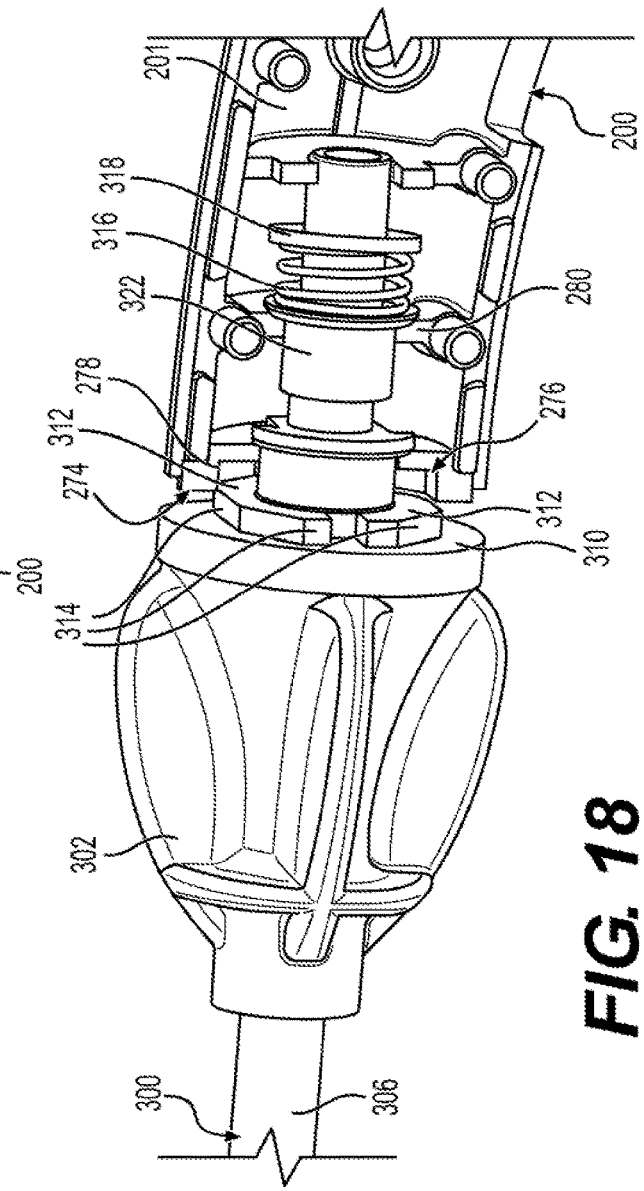
FIG. 18 is a detailed internal perspective view of an example shaft and handle in an unlocked configuration.
Figure 19:
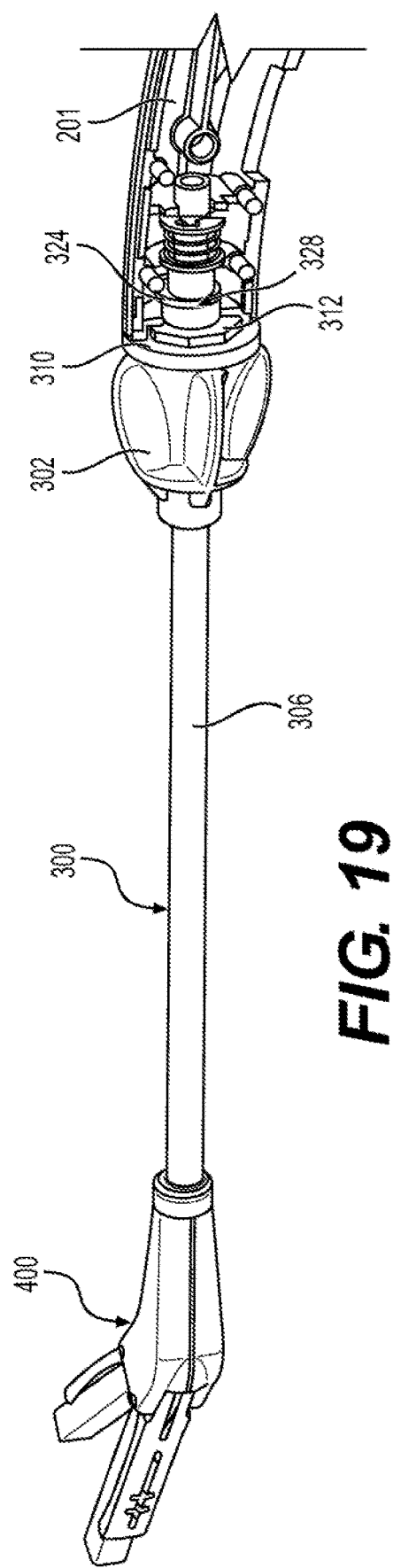
FIG. 19 is an internal perspective view of a distal portion of an example handle with an example shaft in a rotated configuration.

FIG. 15 is a detailed perspective view of a distal portion of an example handle 200, according to at least some aspects of the present disclosure. FIG. 16 is a detailed perspective view of a proximal portion of an example shaft 300, according to at least some aspects of the present disclosure. FIG. 17 is a detailed internal perspective view of an example shaft 300 and handle 200 in a locked configuration, according to at least some aspects of the present disclosure. FIG. 18 is a detailed internal perspective view of an example shaft 300 and handle 200 in an unlocked configuration, according to at least some aspects of the present disclosure. FIG. 19 is an internal perspective view of a distal portion of an example handle with an example shaft in a rotated configuration, according to at least some aspects of the present disclosure.

Referring to FIG. 16, an example shaft 300 may include a generally cylindrical body with a generally longitudinal channel 308 extending therethrough, generally in the form of a tube 306. Activation cable 210 (FIGS. 6-8) and/or deployment cable 250 (FIGS. 11-14) may extend distally through channel 308 of tube 306 from handle 200 to end effector 400. End effector 400 may be disposed on a distal portion of tube 306 and shaft rotation knob 302 may be disposed on a proximal portion of tube 306.

Referring to FIGS. 15-18, handle 200 and shaft rotation knob 302 may include releasably engageable corresponding locking features arranged to selectively inhibit rotation of shaft 300 with respect to handle 200. Referring to FIG. 15, in some example embodiments, a distal face 274 of handle 200 (e.g., shells 201, 203) may include a locking feature, such as a locking recess 276. Locking recess 276 may include a plurality of generally radially inwardly facing locking faces 278. In some example embodiments, locking recess 276 may be generally octagonally shaped, with eight locking faces 278 disposed substantially evenly circumferentially to at least partially define locking recess 276.

Referring to FIGS. 16-18, in some example embodiments, a proximal face 310 of shaft rotation knob 302 may include a locking feature, such as proximally projecting locking boss 312. Locking boss 312 may include a plurality of generally radially outwardly facing locking faces 314. In some example embodiments, locking boss 312 may be generally octagonally shaped, with eight locking faces 314 disposed substantially evenly circumferentially to at least partially define locking boss 312.

In some example embodiments, locking boss 312 and locking recess 276 may be sized and shaped such that locking boss 312 may be slidably received at least partially within locking recess 276. Respective outwardly facing locking faces 314 of locking boss 312 may generally align with and axially slidably engage with respective inwardly facing locking faces 278 of locking recess 276.

Referring to FIGS. 16-18, shaft 300 may include a compression spring 316 disposed coaxially around tube 306 proximally from shaft rotation knob 302. Spring 316 may be restrained on tube 306 proximally by a retainer, such as retainer clip 318, which may be affixed to tube 306 at circumferential groove 320. At its distal end, spring 316 may press against a bushing 322, which may be slidably disposed coaxially around tube 306 between shaft rotation knob 302 and spring 316 (e.g., proximally of shaft rotation knob 302 and distally of spring 316).

Referring to FIGS. 17 and 18, handle 200 (e.g., shell 201 and/or shell 203) may include a spring stop feature, such as laterally disposed internal wall 280, which may be arranged to engage and oppose distal movement of bushing 322. Spring 316 may press apart bushing 322 and retainer clip 318, which may bias tube 306 in the proximal direction relative to handle 200.

In the locked configuration (FIG. 17), spring 316 may be at least partially extended and locking boss 312 of shaft rotation knob 302 may be at least partially engaged proximally within locking recess 276 of handle 200. Accordingly, rotation of shaft 300 relative to handle 200 may be prevented by the engagement of outwardly facing locking faces 314 of locking boss 312 with respective inwardly facing locking faces 278 of locking recess 276. In some example embodiments, proximal face 310 of shaft rotation knob 302 may contact distal face 274 of handle 200 when shaft rotation knob 302 is in the locked configuration.

To shift from the locked configuration (FIG. 17) to the unlocked configuration (FIG. 18), a user may apply a generally distal force on shaft rotation knob 302, moving shaft 300 distally relative to handle 200 by overcoming the force of spring 316. In the unlocked configuration (FIG. 18), spring 316 may be at least partially compressed and locking boss 312 of shaft rotation knob 302 may be substantially disengaged distally from locking recess 276 of handle 200. Accordingly, shaft 300 may be rotatable with respect to handle 200, such as by a user rotating shaft rotation knob 302.

To shift from the unlocked configuration (FIG. 18) to the locked configuration (FIG. 17), shaft rotation knob 302 moves proximally relative to handle 200 to at least partially engage locking boss 312 of shaft rotation knob 302 within locking recess 276 of handle 200. In some example embodiments, the force exerted by spring 316 may be sufficient to shift from the unlocked configuration to the locked configuration when the user-applied distal force is removed from shaft rotation knob 302.

FIG. 19 shows an example shaft 300 in a rotated configuration with shaft rotation knob 302 in a locked configuration. Compare the position of end effector 400 in FIG. 2 and FIG. 19. In some alternative example embodiments according to at least some aspects of the present disclosure, shaft 300 may be rotatably mounted to handle 200 in a manner that allows the user to adjust the degree of rotation to any angle (within a maximum rotation range) without being limited to locking at predetermined rotation increments. See, for example, FIG. 32 and the corresponding description of an alternative shaft rotation feature including a friction spring, below.

Referring to FIGS. 15-19, in some example embodiments including generally octagonal locking features (e.g., locking recess 276 and/or locking boss 312), shaft 300 may be lockable in angular positions that are about 45 degrees apart. It is within the scope of the present disclosure to utilize corresponding locking features (e.g., locking recess 276 and/or locking boss 312) having shapes other than generally octagonal. For example, corresponding locking features may be generally triangular, square, pentagonal, hexagonal, heptagonal, nonagonal, or decagonal, and/or shaped in general as any other substantially rotationally symmetric polygon.

Referring to FIGS. 15, 16 and 19, an example shaft rotation knob 302 may include a rotation limiting feature, such as a stop 324. Stop 324 may include one or more stop faces 326, 328, which may be disposed to engage a rotation limiting feature, such as generally longitudinally extending bar 282 disposed on handle 200 (e.g., on shell 201), when shaft rotation knob 302 is rotated a predefined maximum desired amount. For example, stop face 326 may engage bar 282 and prevent further rotation when shaft rotation knob 302 is rotated about 90 degrees clockwise when looking distally. Stop face 328 may engage bar 282 and prevent further rotation when shaft rotation knob 302 is rotated about 90 degrees counterclockwise when looking distally. Accordingly, in some example embodiments, shaft rotation knob 302 (and shaft 300) may be rotatable over about 180 degrees. In some example embodiments including generally octagonal locking features (e.g., locking recess 276 and/or locking boss 312) and rotation limiting features allowing about 180 degrees of rotation, shaft 300 may be lockable in five angular positions that are about 45 degrees apart.

In some example embodiments, rotation of shaft 300 may be inhibited when clip applier 100 is in the open configuration (FIG. 2). For example, when activation lever 204 is in the open configuration, activation cable 210 may be pulled tight, which may prevent distal movement of shaft 300 relative to handle 200. Accordingly, shifting from the locked configuration (FIG. 17) to the unlocked configuration (FIG. 18) may be prevented.

FIG. 20 is a side elevation view of clip applier 100 with shaft 300 in a bent configuration, according to at least some aspects of the present disclosure. In some example embodiments, shaft 300 may malleable (e.g., plastically deformable) such that it may be reshaped by a user to adapt the shape of shaft 300 to better accommodate specific patient anatomies. For example, shaft 300 may be configured to permit adjustment by bending at an angle 304 with respect to an unbent configuration (e.g., FIG. 2). In some example embodiments, shaft 300 may be configured to allow bending up to an angle 304 of about 45 degrees in any direction. Some example clip appliers 100 may be configured by a user to adapt to specific patient anatomies by both rotating shaft 300 and bending shaft 300. In some example embodiments, shaft 300 may be bent in different shapes, may be bent in more than one direction, and/or may be bent in any manner necessary to provide enhanced access to the occlusion site of a particular patient.

In some example embodiments, shaft 300 may be constructed of a material with a relatively low yield strength and a high elongation percentage. For example, 1100 aluminum may have a yield strength of about 5,000 psi and/or may have an elongation percentage of about 35%, 3003 aluminum may have a yield strength of about 6,000 psi and/or an elongation percentage of about 30%. 5052 Aluminum) One of skill in the art will recognize that selecting a material with a particular yield strength in conjunction with the dimensions of the shaft may achieve desired properties. For example, some embodiments may be configured to permit bending by hand and retaining the shape (e.g., plastically deforming the shaft). In some example embodiments, selecting a material with a high elongation percentage may allow multiple bends without breaking. In some example embodiments, the shaft 300 material may have a strength less than about 28,000 psi and/or may have an elongation percentage greater than about 12%. In some example embodiments, shaft 300 may be constructed of other metals, such as aluminum 5052, copper, stainless steel (e.g., annealed thin walled). In some example embodiments, shaft 300 may be constructed of deformable plastic, such as polycarbonate.

The following description includes various alternative example features and embodiments. One of skill in the art will recognize that these and other alternative example features and embodiments may be used in addition to and/or in place of various features and embodiments described elsewhere in the present disclosure.

Figure 21:
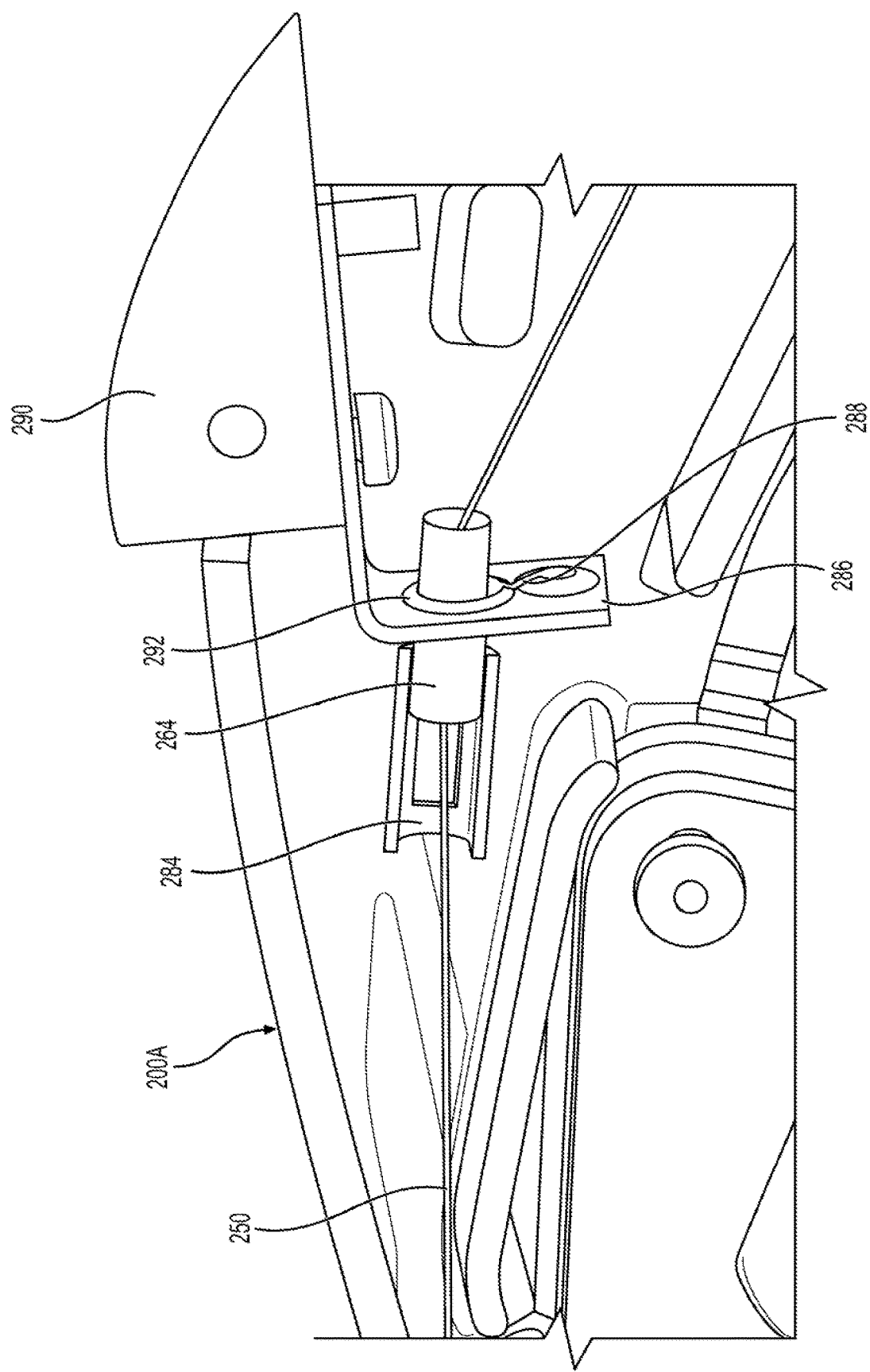
FIG. 21 is a detailed internal perspective view of alternative example occlusion clip release components in a during deployment configuration.

FIG. 21 is a detailed internal perspective view of alternative example occlusion clip release components in a during deployment configuration. In some example embodiments, crimp sleeve 264 on deployment cable 250 may be longitudinally slidably disposed within, but restrained laterally by, a fixed slot 284, which may be fixedly disposed inside handle 200A. A movable anchoring plate 286 including a slot 288 may be arranged to prevent proximal movement of crimp sleeve 264 in a before deployment configuration. For example, crimp sleeve 264 may at least partially abut anchoring plate 286. A user-activated deployment trigger, such as deployment button 290 may be pivotably disposed on handle 200A and may be operatively coupled to anchoring plate 286. Upon actuation of deployment button 290, such as by it being pressed by a user's thumb, anchoring plate 286 may move to the during deployment configuration shown in FIG. 21, in which an opening 292 is aligned with crimp sleeve 264, allowing crimp sleeve 264 to move proximally relative to fixed slot 284 and/or anchoring plate 286. For example, crimp sleeve 264 may move at least partially through opening 292 of anchoring plate 286. In some example embodiments, the other occlusion clip release components may operate substantially similarly to those described in connection with FIGS. 11-13.

Figure 22:
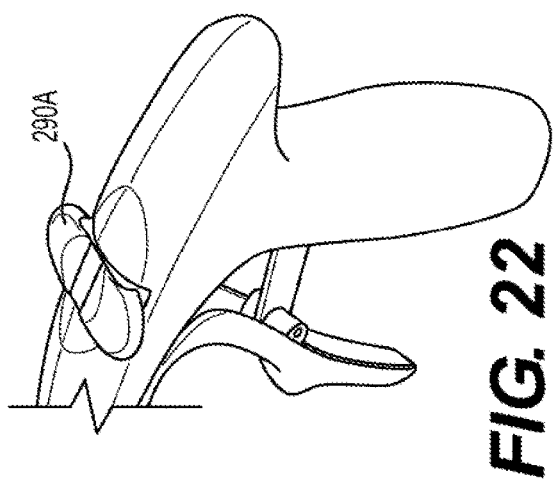
FIG. 22 is a perspective view of an alternative example deployment button.
Figure 23:
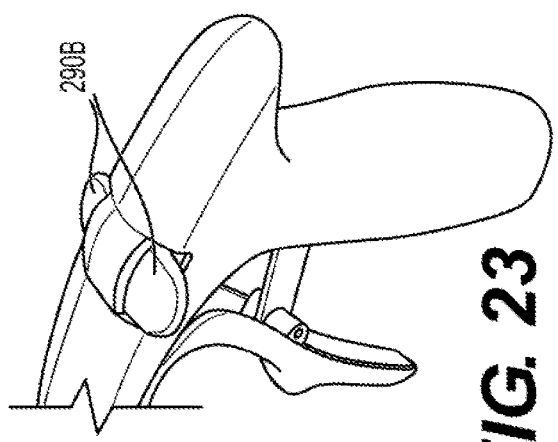
FIG. 23 is a perspective view of an alternative example deployment button.
Figure 24:
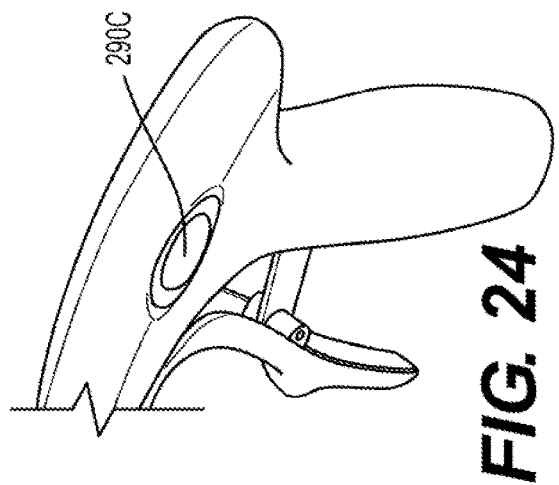
FIG. 24 is a perspective view of an alternative example deployment button.

FIGS. 22-24 are perspective views, according to at least some aspects of the present disclosure, of alternative example locations and configurations for user-activated deployment triggers, such as deployment buttons 290A, 290B, 290C, which may operate substantially similarly to user-activated deployment button 290 described in connection with FIG. 21 or deployment trigger 206 (FIGS. 11-13).

Figure 25:
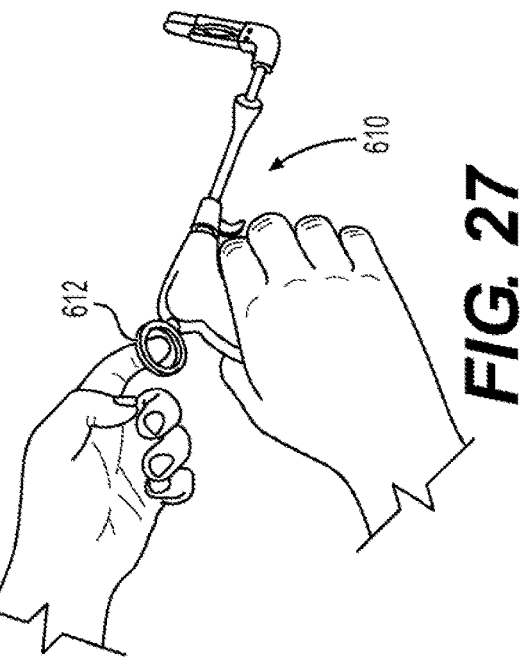
FIG. 25 is a perspective view of an example thumbwheel deployment cable retractor.

FIG. 25 is a perspective view of an alternative example clip applier 600 including a thumbwheel deployment cable retractor 602, according to at least some aspects of the present disclosure. In some alternative embodiments, a thumbwheel retractor mechanism may be used to retract deployment cable 250 in place of a mechanism including deployment trigger 206, anchoring plate 262, and extension spring 256 and related components. Generally, rotation of a thumbwheel 602 (such as by a user's thumb) may retract deployment cable 250. In some example embodiments, a thumbwheel mechanism may facilitate one-handed operation and/or may allow for improved control of the clip applier 600.

Figure 26:
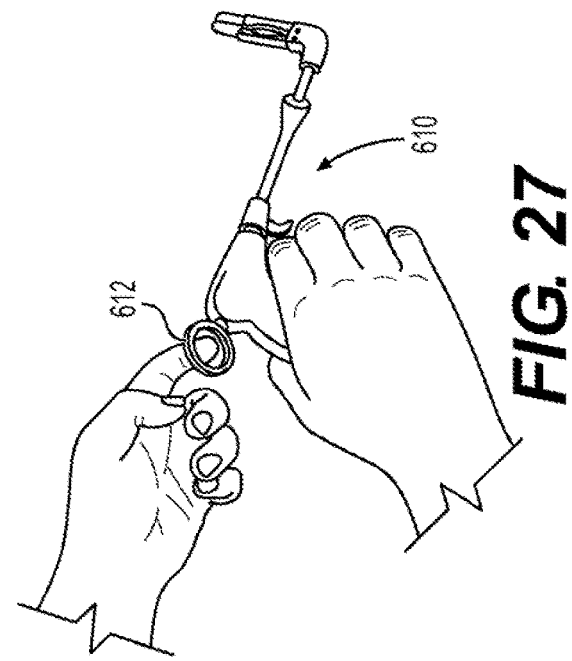
FIG. 26 is a perspective view of an example lever actuated deployment cable retractor.

FIG. 26 is a perspective view of an alternative example clip applier 604 including a lever actuated deployment cable retractor, according to at least some aspects of the present disclosure. In some example embodiments, clip applier 604 may include a deployment lever 606, which may be placed in an ergonomically appropriate location and/or which may be pivoted by a user to retract deployment cable 250. In some example embodiments, a pulley system may be used to increase the stroke length required to retract the cable past the suture loops. Some example embodiments including a lever actuated deployment cable retractor may facilitate one-handed operation and/or improved control of the clip applier 604. In some example embodiments, deployment lever 606 may be disposed in a location that may be protected from inadvertent operation by a trigger guard 608. Similar trigger guards 608 may be used with other example clip appliers according to the present disclosure. In some alternative embodiments, a lever actuated deployment cable retractor may be used to retract deployment cable 250 in place of a mechanism including deployment trigger 206, anchoring plate 262, and extension spring 256 and related components.

Figure 27:
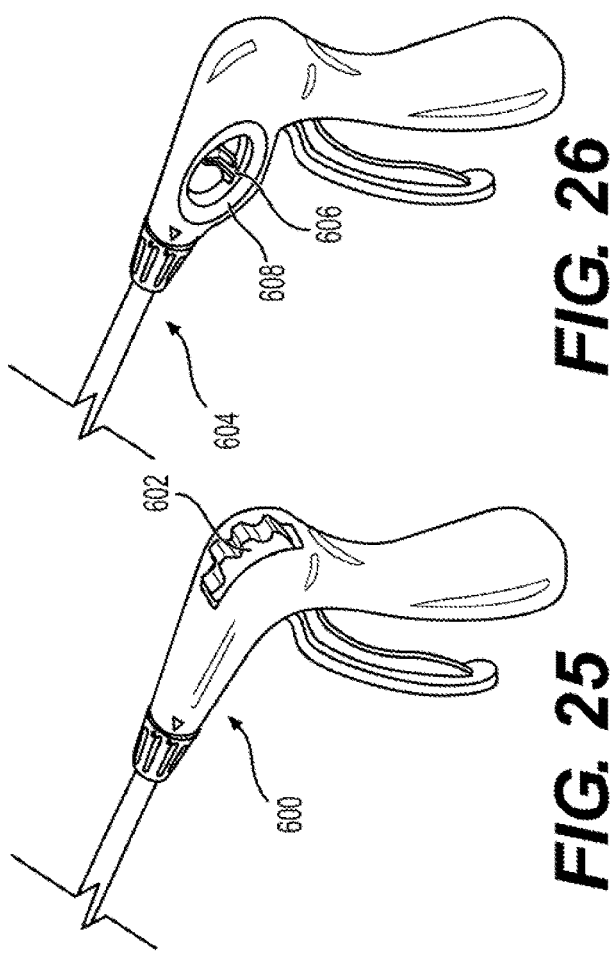
FIG. 27 is a perspective view of an example pull tab deployment cable retractor.

FIG. 27 is a perspective view of an alternative example clip applier 610 including a pull tab 612 deployment cable retractor, according to at least some aspects of the present disclosure. In some example embodiments, pull tab 612 may include a hole that can readily be manipulated, such as with one finger. Pull tab 612 may be actuated using a twisting motion to free (e.g., unlock) pull tab 612. For example, pull tab 612 may be rotated clockwise or counterclockwise by a predetermined amount, which may be about 45 to about 90 degrees. Then, pull tab 612 may be pulled proximally to withdraw deployment cable 250 and release the occlusion device. In some example embodiments, one or more ears of pull tab 612 may lock into the handle when pull tab 612 is in a locked configuration. Turning pull tab 612 may release the ears, allowing a smooth withdrawal of deployment cable 250. In some example embodiments, pull tab 612 may include a detent feature to reduce the risk of inadvertent rotation during shipping and/or use. In some example embodiments, a pull tab 612 using a rotation motion for unlocking and a proximal motion for cable 250 withdrawal may provide improved ergonomics and/or may reduce a jerking motion experienced with some clip appliers that use a straight pull unlocking motion. In some alternative embodiments, a pull tab deployment cable retractor may be used to retract deployment cable 250 in place of a mechanism including deployment trigger 206, anchoring plate 262, and extension spring 256 and related components.

Figure 28:
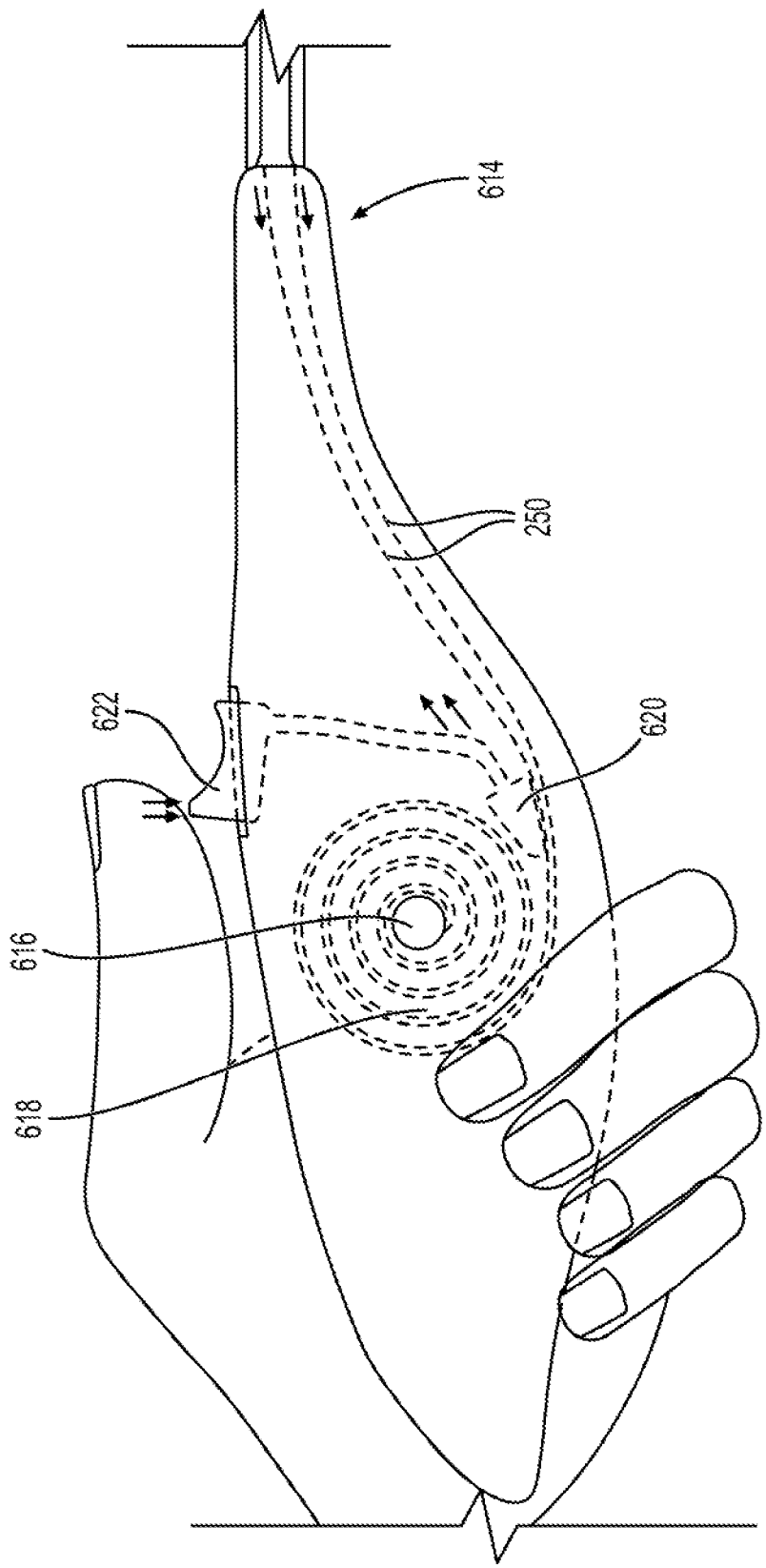
FIG. 28 is a side elevation view of an alternative example clip applier including a torsion spring cable retractor.

FIG. 28 is a side elevation view of an alternative example clip applier 614 including a torsion spring cable retractor, according to at least some aspects of the present disclosure. Some example embodiments may operate generally similar to a retractable tape measure. In some example embodiments, a torsion spring 616 may be operatively coupled to a spool 618, which may receive deployment cable 250. Clip applier 614 may be provided with torsion spring 616 pre-torsioned so that spool 618 applies proximal tension on deployment cable 250. A retainer 620 may selectively prevent proximal withdrawal (e.g., retraction) of deployment cable 250 until retainer 620 is disengaged by a user, such as by pressing a deployment button 622. In some alternative embodiments, a torsion spring cable retractor may be used to retract deployment cable 250 in place of a mechanism including deployment trigger 206, anchoring plate 262, and extension spring 256 and related components. It is within the scope of the present disclosure to utilize a torsion spring cable retractor in an occlusion device application with any handle style, including pistol grip, plunger, and/or ambidextrous handheld.

Figure 30:
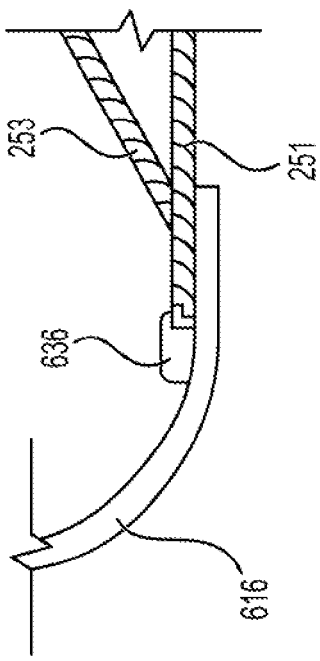
FIG. 30 is side elevation view of an example solder method of attaching a deployment cable to a torsion spring.
Figure 31:
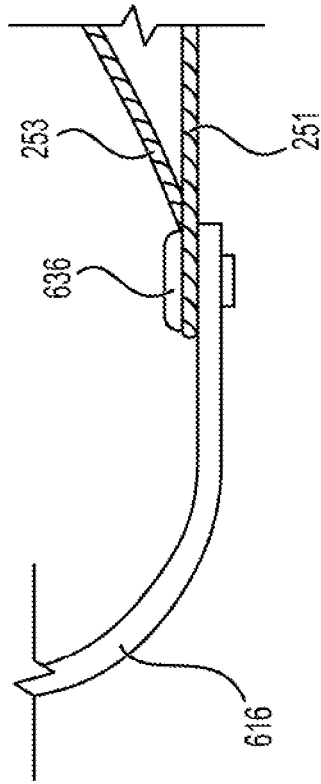
FIG. 31 is side elevation view of an example fastener method of attaching a deployment cable to a torsion spring.
Figure 29:
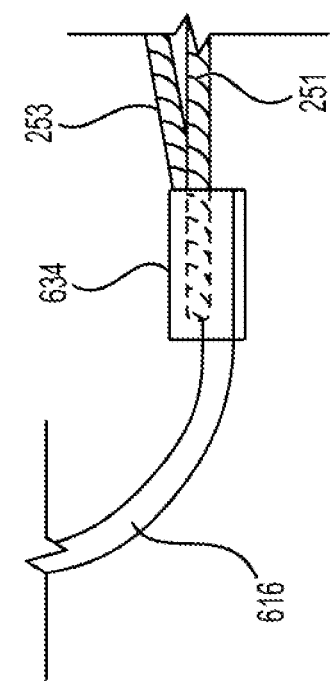
FIG. 29 is side elevation view of an example crimp plate method of attaching a deployment cable to a torsion spring.

FIGS. 29-31 are side elevation views of example methods for attaching strands 251, 253 of deployment cable 250 to torsion spring 616, according to at least some aspects of the present disclosure. FIG. 29 illustrates attachment using a crimp plate 634, which may couple strands 251, 253 of deployment cable 250 to torsion spring 616. FIG. 30 illustrates attachment using solder 636, which may couple strands 251, 253 of deployment cable 250 to torsion spring 616. FIG. 31 illustrates attachment using a fastener 638 (such as a rivet or similar fastener), which may couple strands 251, 253 of deployment cable 250 to torsion spring 616.

Figure 32:
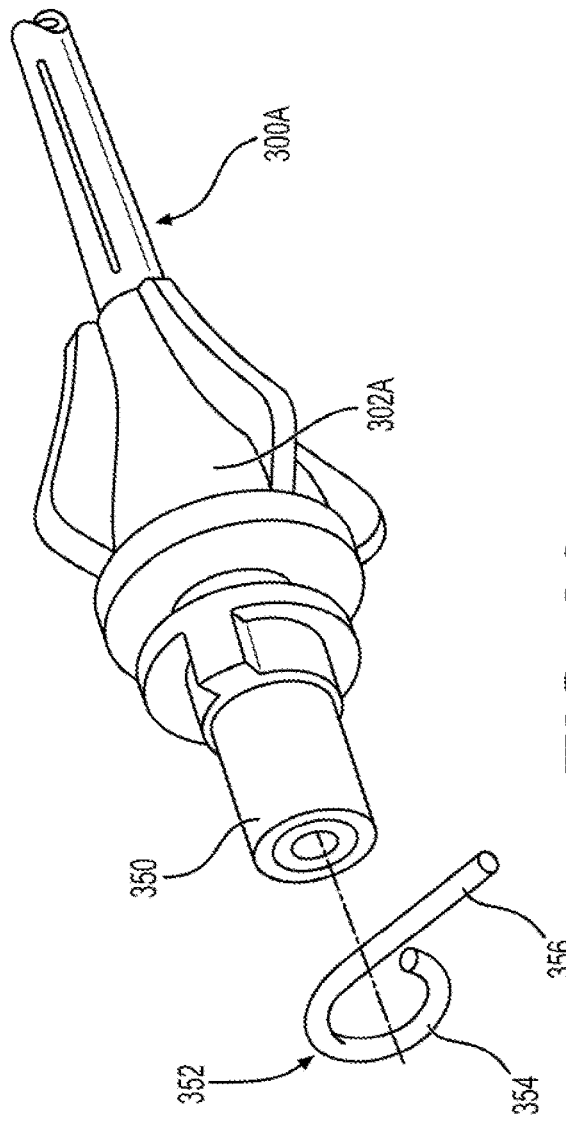
FIG. 32 is a detailed perspective view of an alternative shaft rotation feature including a friction spring.

FIG. 32 is a detailed perspective view of an alternative shaft rotation feature including a friction spring, according to at least some aspects of the present disclosure. In some example embodiments, a proximal portion of shaft 300A (such as proximal portion of shaft rotation knob 302A) may include an outer surface 350, which may be configured to receive a looped section 354 of friction spring 352 thereabout. A tangentially extending tab 356 of spring may engage an internal feature of handle 200 to prevent rotation of spring 352 relative to shells 201, 203. The fit of loop section 354 of friction spring 352 on surface 350 may be a press fit (e.g., about 0.010"), which may provide sufficient friction between loop section 354 and surface 350 to reduce unwanted rotation but may allow a user to rotate shaft 300A by rotating shaft rotation knob 302A with sufficient torque when desired. One of skill in the art that the friction may be increased or decreased based on the diameter of the spring and/or by the press fit dimension. In some example embodiments, utilizing a friction spring shaft rotation feature may be desirable because it may not require additional controls or parts to facilitate rotation of shaft 300A. In some alternative embodiments, a friction spring shaft rotation feature may be used in place of a mechanism including locking recess 276, locking boss 312, and/or related components.

Figure 33:
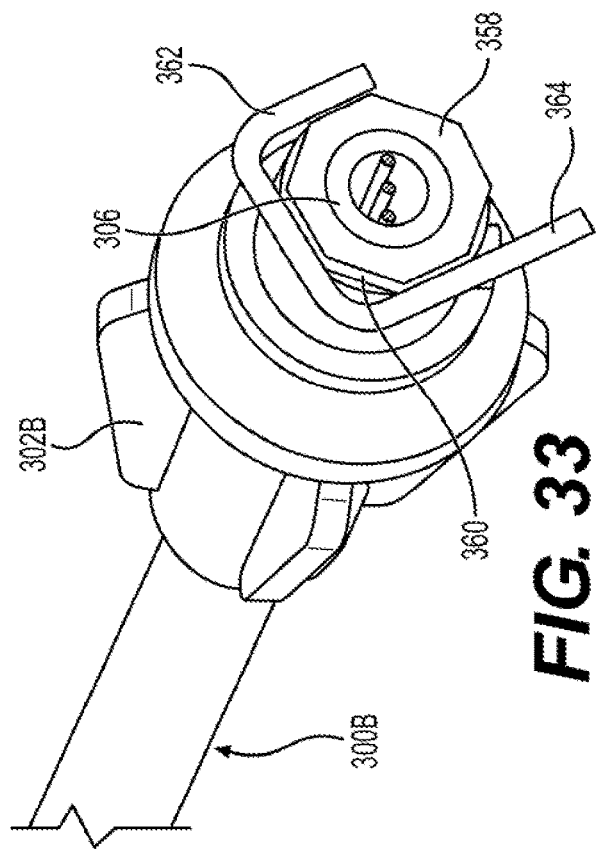
FIG. 33 is a detailed perspective view of an alternative shaft rotation feature including a detent mechanism.

FIG. 33 is a detailed perspective view of an alternative shaft rotation feature including a detent mechanism, according to at least some aspects of the present disclosure. In some example embodiments, a proximal end of shaft rotation knob 302B disposed on a shaft 300B may include a proximally extending lock projection 358, which may include a plurality of faces 360. A locking spring 362 may elastically engage one or more faces 360. Locking spring 362 may include a tangentially extending tab 364 that may engage an internal feature of handle 200 such that spring 362 is not rotatable relative to handle 200. In some example embodiments, the engagement of locking spring 362 with one or more faces 360 may reduce unwanted rotation of shaft 300B but may allow a user to rotate shaft 300B by rotating shaft rotation knob 302B with sufficient torque to overcome locking spring 362 when desired. When rotated by a user, locking spring 362 may elastically deform to allow rotation of lock projection 358, disengaging from one face 360, then elastically engaging an adjacent face 360. In some example embodiments, utilizing a detent mechanism shaft rotation feature may be desirable because it may not require additional controls or parts to facilitate rotation of shaft 300B. In some alternative embodiments, a detent mechanism shaft rotation feature may be used in place of a mechanism including locking recess 276, locking boss 312, and/or related components.

Some example embodiments may include a removable safety device arranged to prevent deployment of an occlusion clip prior to the intended deployment. For example, a safety device may reduce the likelihood of accidental deployment of the occlusion clip during manufacture, inspection, transit, and/or handling. FIG. 34 is a perspective view of an example clip applier including a lateral safety tab 624 according to at least some aspects of the present disclosure. Lateral safety tab 624 may include an outwardly extending grip 626 that may be grasped by a user coupled to a laterally extending pin 628, which may extend at least partially into and/or through handle 200B. Pin 628 may releasably engage the occlusion clip deployment mechanism within handle 200B to block operation of the user-activated trigger or button and/or prevent actuation of the mechanism until lateral safety tab 624 is withdrawn laterally from handle 200B.

FIG. 35 is a perspective view of an example clip applier including a longitudinal safety tab 630 according to at least some aspects of the present disclosure. Longitudinal safety tab 630 may include an outwardly extending grip 632 that may be grasped by a user coupled to a longitudinally extending portion (e.g., a pin) (not shown), which may extend at least partially into and/or through handle 200C. Safety tab 630 may releasably engage the occlusion clip deployment mechanism within handle 200C to block operation of the user-activated trigger or button and/or prevent actuation of the mechanism until longitudinal safety tab 630 is withdrawn longitudinally from handle 200C.

In some example embodiments, safety tabs 624, 630 may be easily identifiable, such as by color or other markings. In some example embodiments, a safety tab 624, 630 may block operation of the clip deployment mechanism (in addition to blocking operation of the user-activated trigger or button), which may inhibit inadvertent actuation of the deployment mechanism due to inertia, such as if the clip applier is dropped.

FIGS. 36-37 are interior perspective views of example shells 201, 203 of handle 200, according to at least some aspects of the present disclosure. As described elsewhere in the present disclosure, shells 201, 203 may include bearings 205, 207, 209, 211, boss 258, anchoring plate slots 213, 215, track 226, first sidewall 228, second sidewall 230, wall 280, and/or bar 282.

U.S. Pat. No. 9,901,352, titled "Occlusion Clip" and incorporated herein by reference, describes example occlusion clips that may be used with at least some embodiments according to the present disclosure. Some example embodiments according to at least some aspects of the present disclosure may be configured for use with clips that are open-ended, closed-biased, and/or close tip-first. Some example embodiments may be used with closed-ended occlusion clips.

In some example embodiments, clip applier 100 may be a single-use (e.g., disposable) device and/or occlusion clip 1000 may be provided pre-loaded on clip applier 100. Some example clip appliers 100 may be provided with pre-loaded occlusion clips 1000 of different sizes, allowing a user to select an appropriate clip applier 100 with pre-loaded clip 1000 of a size appropriate for a particular patient. For example, a selection of clip appliers 100 having a pre-loaded occlusion clips 1000 that are 35 mm, 40 mm, 45 mm, and/or 50 mm in size may be provided.

The present disclosure contemplates that some medical devices, such as some example clip appliers 100 according to the present disclosure, may require sterilization prior to use. Accordingly, some example embodiments may be constructed from materials that may be compatible with various sterilization methods, such as gamma sterilization. For example, handle shells 201, 203, activation lever 204, deployment trigger 206, and/or shaft rotation knob 302 may be constructed from injection molded plastic. For example, shaft 300, linkage 212, activation cable 210, deployment cable 250, crimp sleeves 222, 264, extension spring 256, and/or anchoring plate 260 may be constructed from metals. In some example embodiments, metals may be selected to provide corrosion resistance, such as aluminum and/or stainless steel. In some example embodiments, metals may receive surface treatments, such as anodization and/or passivation, to provided added corrosion resistance.

It is within the scope of the present disclosure to utilize the apparatus and methods described herein in connection with any anatomical structure that may be occluded, including anatomical structures other than LAAs.

Following from the above description and invention summaries, it should be apparent to those of ordinary skill in the art that, while the methods and apparatuses herein described constitute example embodiments according to the present disclosure, it is to be understood that the scope of the disclosure contained herein is not limited to the above precise embodiments and that changes may be made without departing from the scope as defined by the following claims. Likewise, it is to be understood that it is not necessary to meet any or all of the identified advantages or objects disclosed herein in order to fall within the scope of the claims, since inherent and/or unforeseen advantages may exist even though they may not have been explicitly discussed herein.

What is claimed is:

1. A medical instrument, comprising:
   a handle;
   a deployment trigger disposed on the handle, the deployment trigger being movable between a pre-deployment configuration and a deployment configuration by application of an external force to the deployment trigger;
   a shaft mounted to and extending distally from the handle;
   an end effector disposed distally on the shaft, the end effector comprising a first jaw configured to releasably receive an occlusion clip, the deployment trigger being operatively coupled to the first jaw by a deployment cable; and
   an elastic member disposed within the handle, the elastic member including a first end and a second end, the second end being affixed to the handle;
   wherein moving the deployment trigger from the pre-deployment configuration to the deployment configuration retracts the deployment cable proximally, releasing the occlusion clip from the first jaw;
   wherein the deployment cable extends from the first end of the elastic member to the first jaw;
   wherein, when the deployment trigger is in the pre-deployment configuration, the elastic member is held in an extended configuration;
   wherein, when the deployment trigger is moved to the deployment configuration, the elastic member retracts the deployment cable proximally; and
   wherein, retracting the deployment cable proximally releases the occlusion clip from the first jaw.

2. The medical instrument of claim 1,
   further comprising
   a stop member affixed to the deployment cable between the first end of the elastic member and the shaft; and
   an anchoring plate disposed within the handle and arranged to selectively block proximal movement of the stop member;
   wherein, when the deployment trigger is in the pre-deployment configuration, the elastic member is held in the extended configuration by the stop member abutting a distal surface of an anchoring plate.

3. The medical instrument of claim 2,
   further comprising a deployment trigger slot disposed on the deployment trigger, the slot slidably receiving the stop member therein;
   wherein the anchoring plate is fixedly mounted to the handle;
   wherein, when the deployment trigger is in the pre-deployment configuration, the deployment trigger slot is at least partially aligned with the anchoring plate; and
   wherein, when the deployment trigger is in the deployment configuration, the deployment trigger slot is aligned generally adjacent to the anchoring plate, thereby allowing the stop member to move proximally relative to the deployment trigger slot and the anchoring plate.

4. The medical instrument of claim 2,
   further comprising a fixed slot disposed on the handle, the slot slidably receiving the stop member therein;
   wherein the anchoring plate is movable relative to the fixed slot;
   wherein the deployment trigger is operatively coupled to the anchoring plate;
   wherein, when the deployment trigger is in the pre-deployment configuration, the fixed slot is aligned such that the stop member at least partially abuts the anchoring plate; and
   wherein, when the deployment trigger is in the deployment configuration, the fixed slot is aligned with an opening through the anchoring plate, thereby allowing the stop member to move proximally relative to the fixed slot and at least partially through the opening through the anchoring plate.

5. The medical instrument of claim 1, further comprising a removable safety tab, the safety tab comprising a pin extending into the handle and arranged to prevent movement of the deployment trigger and a grip extending outwardly from the handle.

6. The medical instrument of claim 1, wherein the handle and the shaft each comprise a releasably engageable corresponding locking feature arranged to selectively inhibit rotation of the shaft relative to the handle.

7. The medical instrument of claim 1, wherein the shaft is plastically deformable up to an angle of at least about 45 degrees.

8. The medical instrument of claim 1,
further comprising an activation lever disposed on the handle, the activation lever being movable between a closed activation lever configuration and an open activation lever configuration by application of an external force to the activation lever;
wherein the first jaw of the end effector is movable between a closed jaw configuration and an open jaw configuration, the first jaw being operatively coupled to the activation lever such that moving the activation lever from the closed activation lever configuration to the open activation lever configuration moves the first jaw from the closed jaw configuration to the open jaw configuration.

9. The medical instrument of claim 3,
wherein the anchoring plate comprises an anchoring plate slot that is wider than the deployment cable and narrower than the stop member; and
wherein, when the deployment trigger is in the pre-deployment configuration, the deployment trigger slot is generally aligned with the anchoring plate slot.

\* \* \* \* \*